(12) United States Patent
Ludl et al.

(10) Patent No.: US 6,847,481 B1
(45) Date of Patent: Jan. 25, 2005

(54) AUTOMATED SLIDE LOADER CASSETTE FOR MICROSCOPE

(75) Inventors: Helmut Ludl, Pound Ridge, NY (US); David Sutton Denu, Yorktown Heights, NY (US)

(73) Assignee: Ludl Electronics Products, Ltd., Hawthorne, NY (US)

(*) Notice: Subject to any disclaimer, the term of this patent is extended or adjusted under 35 U.S.C. 154(b) by 0 days.

(21) Appl. No.: 10/002,545

(22) Filed: Oct. 26, 2001

(51) Int. Cl.⁷ .......................... G02B 21/26; B65B 21/02
(52) U.S. Cl. ...................... 359/391; 359/368; 359/393; 414/416; 414/331
(58) Field of Search ................................. 359/368–390, 359/391–398; 414/416–417, 331, 222–223, 932; 23/865.9

(56) References Cited

U.S. PATENT DOCUMENTS

| | | | |
|---|---|---|---|
| 3,738,730 A | 6/1973 | Binnings et al. ............ 359/391 |
| 3,851,972 A | 12/1974 | Smith et al. ........... 414/225.01 |
| 4,248,498 A | 2/1981 | Georges .................... 359/392 |
| 4,367,915 A | 1/1983 | Georges .................... 359/392 |
| 4,501,495 A | 2/1985 | Faulkner et al. ............ 359/391 |
| 4,807,984 A | 2/1989 | Kurimura et al. ........... 359/393 |
| 4,818,169 A | 4/1989 | Schram et al. ......... 414/331.18 |
| 5,367,401 A | 11/1994 | Saulietis ..................... 359/391 |
| 5,386,318 A | 1/1995 | Kuhnert et al. ............. 359/394 |
| 5,646,776 A * | 7/1997 | Bacchi et al. ............... 359/393 |
| 5,888,042 A * | 3/1999 | Oda ...................... 414/222.07 |
| 6,405,610 B1 * | 6/2002 | Komatsu et al. ........... 73/865.9 |

* cited by examiner

Primary Examiner—Thong Q. Nguyen
(74) Attorney, Agent, or Firm—Collard & Roe, P.C.

(57) ABSTRACT

The slide handler is an instrument that automatically transfers glass microscope slides from a cassette or magazine to a motorized microscope stage and then returns the slide back into the second cassette. The use of this instrument permits the unattended computer control, measurement and inspection of specimens mounted to the slides. Full modular integration of the system components allows for the slide handler instrument to be utilized with any microscope. The instrument system has a minimum of three components; namely a slide cassette indexer, an XY-stage, and a slide exchange arm. The indexer, the arm and the XY-stage are connected together and integrated into one unitary modular instrument that can be moved from one microscope to another.

21 Claims, 21 Drawing Sheets

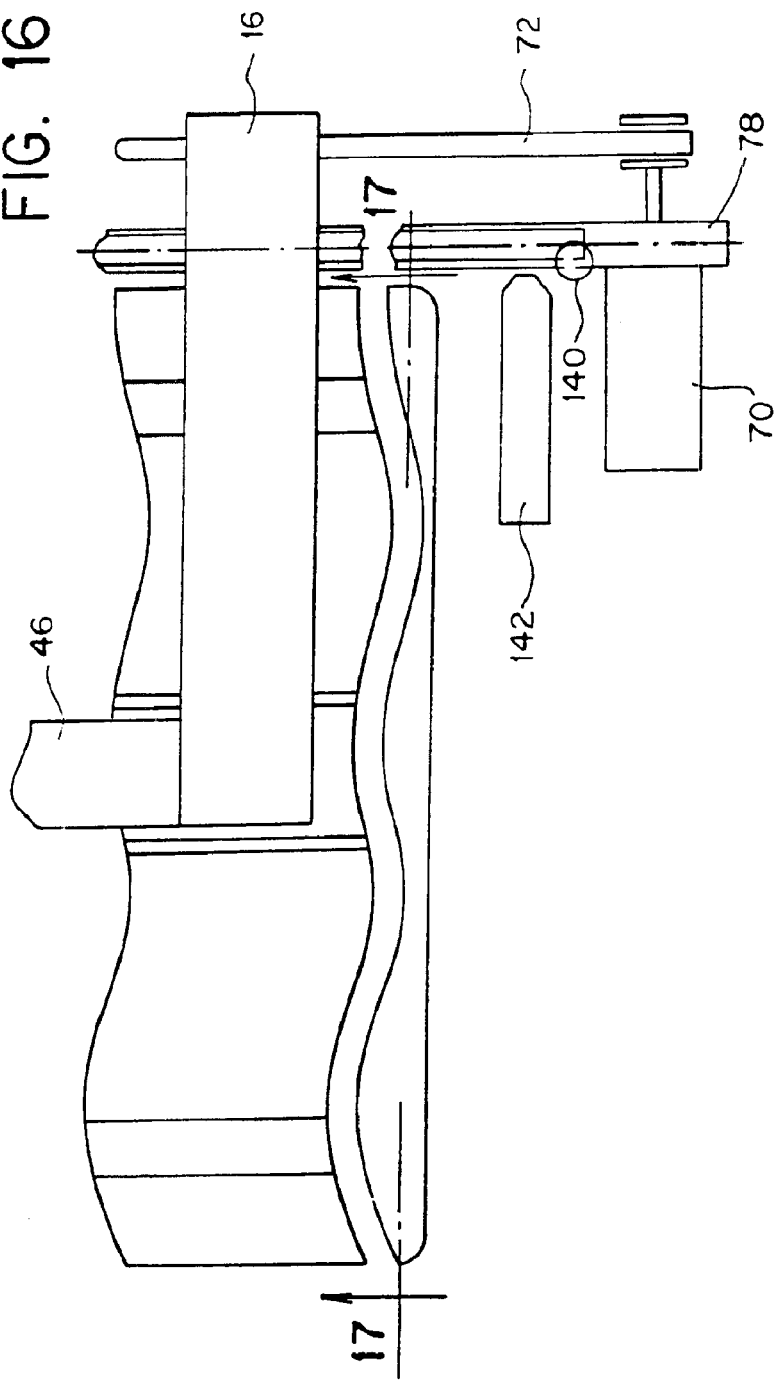
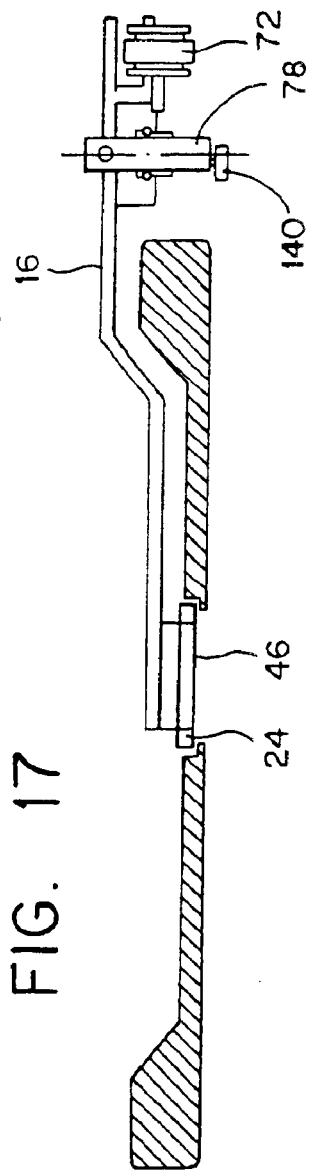

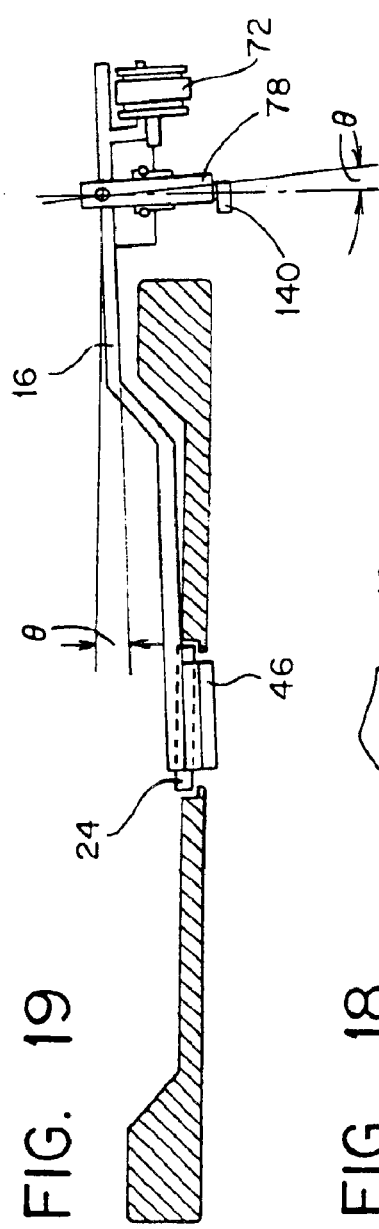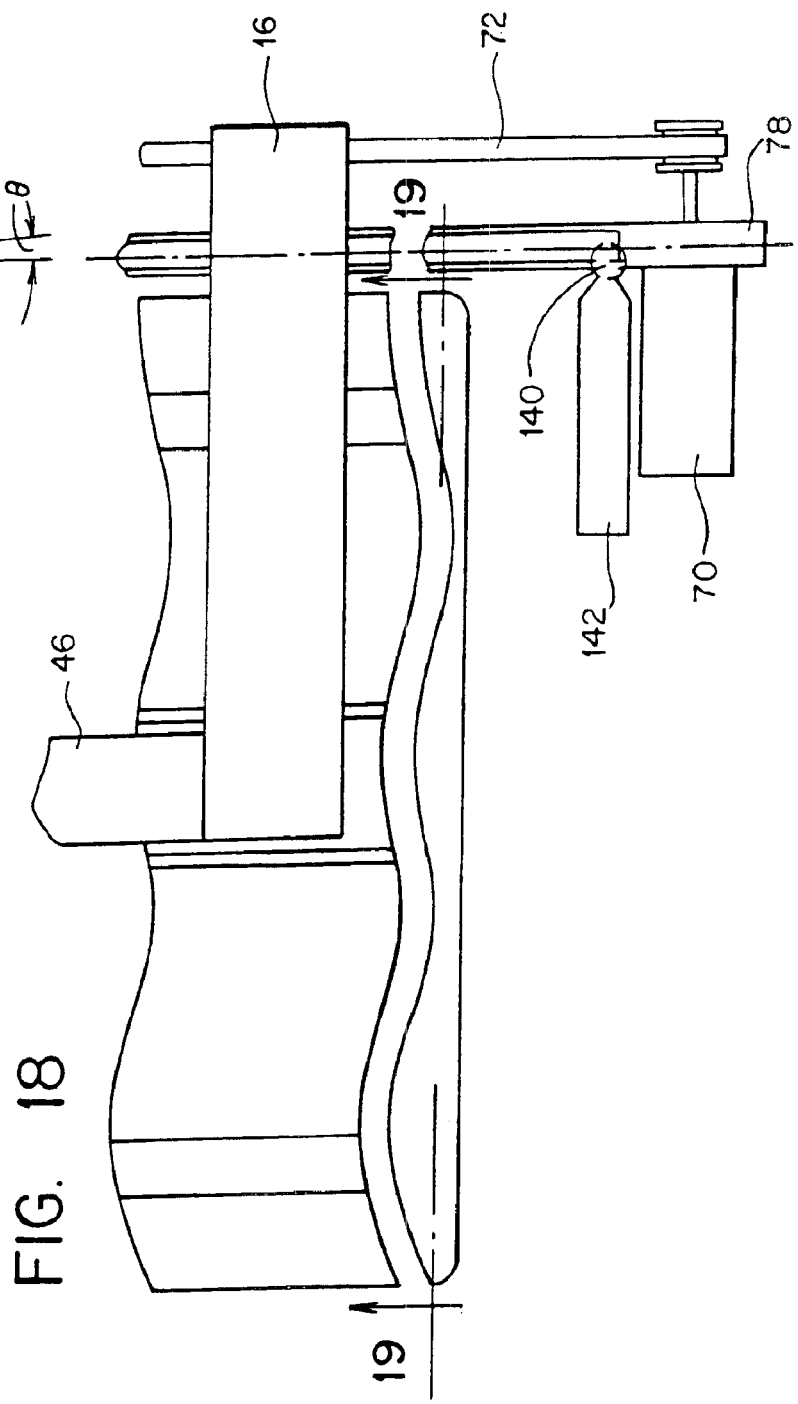

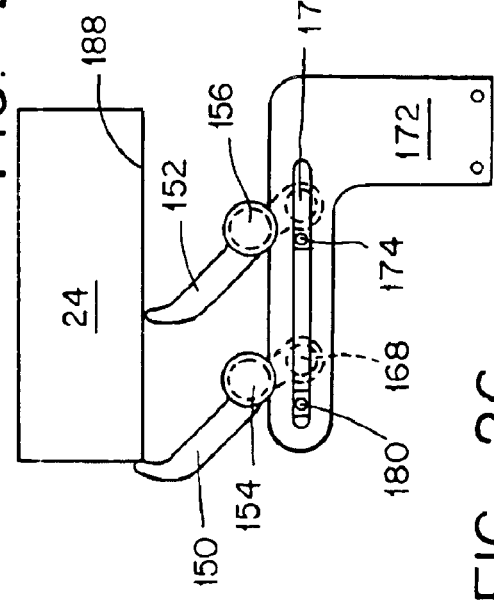
FIG. 23
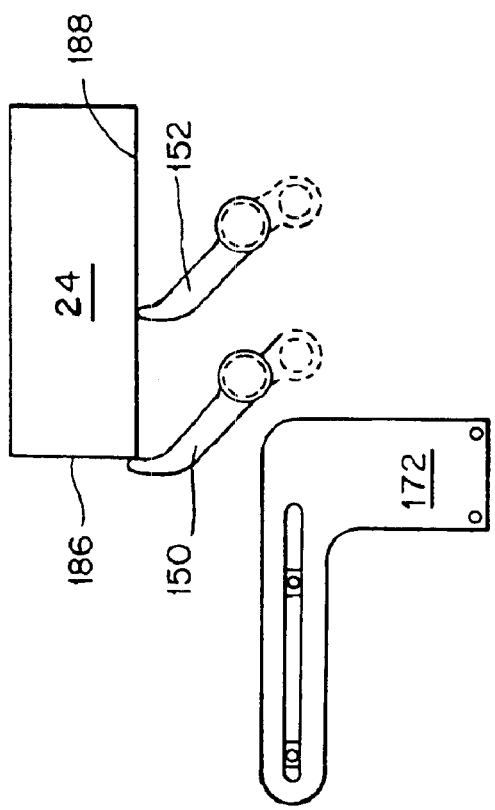
FIG. 25
FIG. 26
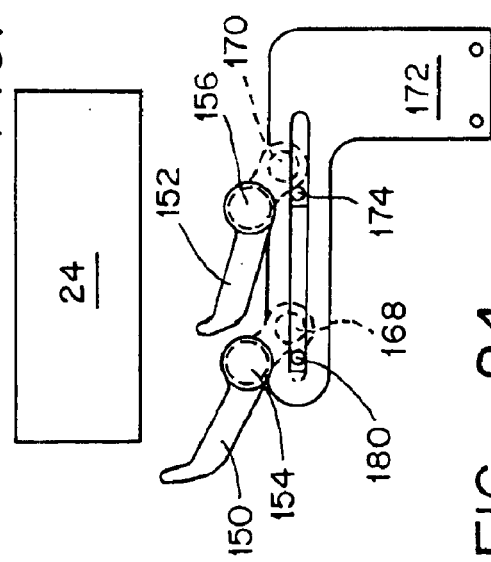
FIG. 24

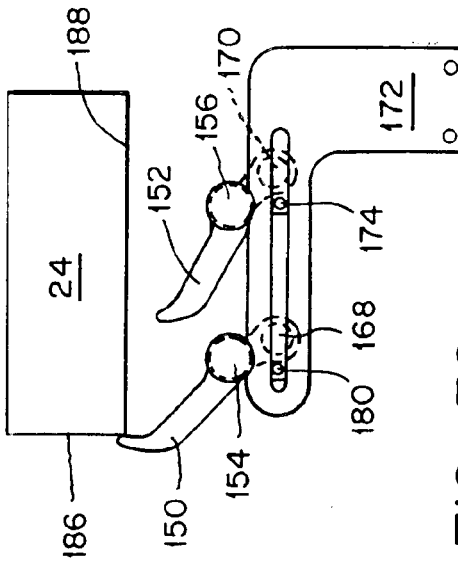
FIG. 27
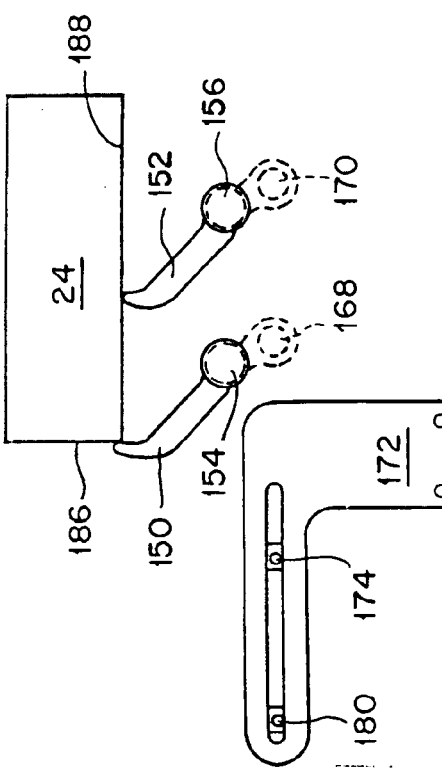
FIG. 28
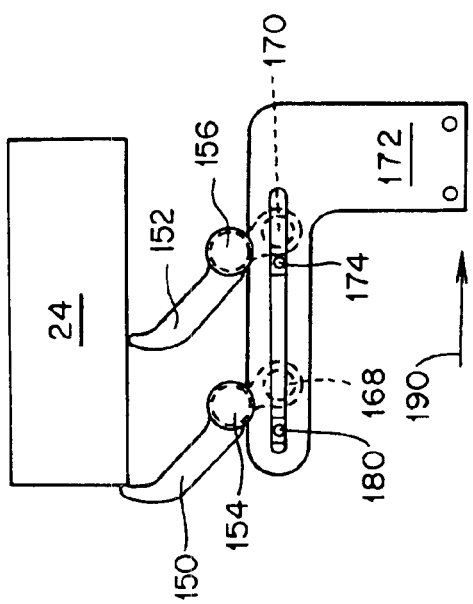
FIG. 29
FIG. 30

AUTOMATED SLIDE LOADER CASSETTE FOR MICROSCOPE

BACKGROUND OF THE INVENTION

1. Field of the Invention

The present invention relates to an automated slide loader cassette for a microscope.

2. The Prior Art

Devices for loading slides from a cassette onto a stage of a microscope are known, as follows.

| U.S. Pat. No. | Patentee | Issue Date |
|---|---|---|
| 3,738,730 | Binnings et al | Jun. 12, 1973 |
| 3,851,972 | Smith et al | Dec. 3, 1974 |
| 4,248,498 | Georges | Feb. 3, 1981 |
| 4,367,915 | Georges | Jan. 11, 1983 |
| 4,501,495 | Faulkner et al | Feb. 26, 1985 |
| 4,807,984 | Kurimura et al | Feb. 28, 1989 |
| 4,818,169 | Schram et al | Apr. 4, 1989 |
| 5,367,401 | Saulietis | Nov. 22, 1994 |
| 5,386,318 | Kuhnert et al | Jan. 31, 1995 |

The above mentioned prior art devices have several disadvantages. For example some of these prior art devices can only withdraw a microscope slide from a holder, but cannot return the slide back into the holder. Other prior art devices are permanently attached to one microscope, and cannot be used with several different microscopes of different size or shape construction. This thereby limits the usefulness of the prior art device.

The disclosure of each of these patent documents is herewith incorporated by reference.

A slide is a microscope slide being a standard 1 inch×3 glass slide or other similar specimen.

SUMMARY OF THE INVENTION

It is an object of the present invention to provide a slide loader which can withdraw a slide from a holder and then return that slide to the same holder.

It is another object of the present invention to provide a slide loader which is modular and can be used with any microscope.

The above objects are achieved according to the present invention by providing an automated slide loader or slide handler instrument for a microscope comprising a slide cassette indexer for containing a plurality of microscope slides; a slide exchange arm for gripping a microscope slide within said indexer and for transporting said slide to said microscope for observation and for transporting said slide after observation to return said slide back into said indexer; and an-XY stage for moving said slide exchange arm between said indexer and said microscope, and positioning the slide for analysis; and said indexer, said arm and said XY-stage are connected together and integrated into one unitary modular instrument that can be moved from one microscope to another.

The above objects are also achieved according to the present invention by providing an automated slide loader or slide handler instrument in combination with a microscope comprising a microscope for individually viewing a plurality of slides one at a time; a slide cassette indexer for containing a plurality of microscope slides; a slide exchange arm for gripping a microscope slide within said indexer and for transporting said slide to said microscope for observation and for transporting said slide after observation to return said slide back into said indexer; an XY stage for moving said slide exchange arm between said indexer and said microscope; and a computer controller for controlling the XY stage; and said indexer, said arm and said XY stage are connected together and integrated into one unitary modular instrument that can be moved from one microscope to another. The XY stage is also used to position and scan the slide for analysis.

The slide handler of the invention is an instrument that automatically transfers glass microscope slides from a cassette or magazine to a motorized microscope stage. The use of this instrument permits the unattended computer controlled measurement and inspection of specimens mounted on the slides. Full modular integration of the system components allows for the slide handler instrument to be utilized with any microscope.

The slide handler instrument of the invention has a minimum of three components; namely a slide cassette indexer, an XY stage, and a slide exchange arm. The three components are connected together and are integrated into one unitary modular instrument that can be moved from one microscope to another.

The slide cassette indexer provides a single vertical axis (the Z-axis) along which is moved the cassette to the proper height for slide transfer. The indexer is mounted on a common, stable base-plate. The base-plate also supports the microscope so that the orientation of the indexer and microscope remains fixed. The slide cassette indexer is actuated by motor driven (either as a stepper motor or as a DC servo motor) leadscrew with electrical and mechanical limits at either end of travel. The indexer is identified as having a vertical or Z-axis.

The XY-stage is a motorized XY-stage. The stage is removably mounted to the microscope with temporary attachment means in such a way that there is no interference with any optics or optical operation of the microscope. By not modifying the microscope, full use of all optical techniques is retained with the slide handling system. The XY-stage is driven in the X-axis direction and in the Y-axis direction by a leadscrew or by rack and pinion gears. The motors used for X direction movement or for Y direction movement can be either stepper motors or DC servomotors. The XY-stage also features an integrated, spring loaded slide retention device that locates the slide relative to a fixed position. The retention device is actively disengaged by mechanical linkage when the XY-stage moves to the slide exchange position.

The remaining component is the slide exchange arm. Mounted on the XY-stage, the arm features a distal finger that manipulates the slide by removal of the slide from the cassette and movement of the slide to the proper position on the XY-stage. Subsequently the arm returns the slide back into the cassette. The arm has a long travel axis that is parallel to the X-axis of the XY-stage; this long travel axis of the arm is defined as the R-axis, or radius axis. The arm also features a short lift travel axis that allows it to completely disengage the slide; this short lift axis of the arm is the T-axis. The T-axis has two defined positions: engaged and disengaged. The arm is driven along the R-axis direction by a motor driven belt with end-limits. The T-axis movement is actuated by mechanical linkage to coordinated motion from the stage X-axis.

The slide handler instrument or system of the invention is designed to accommodate the microscope and the microscope's requirements. The system is removably connected with the microscope and the microscope stage, but it does not interfere with or limit the optical techniques commonly used in laboratory and research environments.

The principal applications for the slide handler system of the invention are in clinical research and pharmaceutical laboratories. To a lesser degree this system can be used by handicapped individuals who would not normally have the dexterity to load a microscope slide.

A conventional computer controller commands the slide handler system in conjunction with a measurement, a recording or an analysis process. Frequently, the specimen on the slide is either a one of a kind sample, or the product of a unique experiment or an actual sample from a patient. Since the slide specimens can have a very high intrinsic value, the slide handler will not damage nor break the slides.

The slide handler system of the invention enables the user to have an unlimited choice of microscopes. The choice of microscope is made for many reasons, such as personal preference, established inventory of like branded accessories, unique capabilities and sales/service support. The slide handler of the invention can be integrated with any microscope and can be temporarily installed onto any microscope. Then the slide handler can be removed from this microscope and installed onto a different microscope.

The advantages of the slide handling system of the invention include: unattended operation; fail-safe operation that will not damage the slides; low cost; simple setup and programming; and easy mounting to an existing microscope without modification of the microscope, and then transfer from one microscope to another.

The slide handler system of the invention is fully integrated with the microscope, and the system uses a single arm to fetch and to replace a slide. By enabling the arm to move freely beneath the slide, the arm has a dual function both to fetch and to replace slides from the vertical slide cassette. The microscope slide is guided in an open-ended channel on the XY-stage. The channel serves to align to slide into position as well as to hold it in place. An adjustable mount makes the slide fixture adjustable so that optical focus is maintained across the entire slide.

Dual slide retaining levers ensure that the slide is in the proper position. The levers are sequenced to contact the slide. The first lever aligns the slide to the edge of the channel, while the second lever assures that the slide is firmly held in position. This is an important feature in that each slide in the sequence of slides can be placed repeatedly on the XY-stage with only a negligible error occurring. Thus the slide location is highly accurate and repeatable for each slide. The construction is such that the slide handler can accommodate slides of varying width, length, and thickness without modification and in most cases without adjustment. This feature enables the slide handler system to be used with slides from different manufacturers on different microscopes without any difficulty.

The construction of the transfer mechanism keeps the slide profile very low, thereby allowing full swing movement for the microscope turrets. This feature and a unique universal XY-stage temporary mounting means make it adaptable to almost any microscope. The transfer arm has sensors for detecting any obstruction in either the slide placement or the slide retrieval. Obstruction detection utilizes a spring-loaded linear clutch that will release when a slide becomes jammed. When the clutch is released, sensor switches will cause the motor to halt and trigger an error. This system also monitors motor position and loads to detect obstructions or failures. This feature will eliminate the likelihood of slide breakage. The system is expandable to include full microscope automation by virtue of the modularity of the control system and accessories. Full automation includes lamp intensity control, programmable optical filters, motorized focus and video auto-focus.

Random cassette slot access allows for the slide handler system to replace the slide in a slot other than the original slot. This enables applications that require sorting and classification. Modular assembly facilities promote installation/alignment, troubleshooting and repair. The major components: exchange arm, XY-stage and indexer are connected together and can be readily moved from one microscope to another. Manual interaction with the XY-stage is maintained. Once the slide is loaded, an XY joystick can optionally be used allowing the operator to manually navigate, focus and position the stage, by overriding the computer control. Then the operation can be returned to automated computer control. Loading the slide manually is also a possibility; however, automated movement is preferred.

The method of operation of the slide handler system is as follows. The sequence to load a slide is as follows. The XY stage moves to a defined load position for the specified cassette. The indexer moves to a vertical position slightly above the specified slot. The slide exchange arm moves into the space beneath the slot. The indexer lowers the slide into the arm. The exchange arm R-axis moves the slide out of the cassette slot into the channel on the XY-stage, locating the slide near the fixture point. The XY-stage moves to a defined position to activate the linkage of the T-axis in sequence to lower the slide exchange arm to a safe level (disengaged) for retraction. The slide exchange arm retracts to a position which is clear of the slide. The XY-stage then moves from the T-axis actuation point to return the exchange arm to the relaxed, engaged position clear of any interference with the optical functions of the microscope.

The sequence of motion to unload a slide is as follows. The XY-stage moves to a defined unload position for the specified cassette, disengaging the retaining arms. The indexer is positioned to the specified cassette slot. The slide exchange arm pushes the slide from the XY-stage into the cassette slot. The arm then retracts to an intermediate position clear of the cassette and the indexer.

An alternate sequence of motion to unload a slide is as follows. The XY-stage moves to an intermediate position to disengage the retaining arms and sequentially to lower the slide exchange arm. The XY-stage moves to a defined unload position for the specified cassette, at the same time raising the arm to support the slide. The indexer is positioned to the specified cassette slot. The slide exchange arm carries the slide from the XY-stage to the cassette slot. The slide indexer raises to remove the slide from the arm. The arm retracts to a safe position.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

FIG. 16 shows a top view of the slide exchange arm assembly engaging and supporting the slide;

FIG. 17 shows a partial section view of the exchange arm assembly along line 17—17 of FIG. 16;

FIG. 18 shows a top view of the slide exchange arm assembly disengaged from and not supporting the slide;

FIG. 19 shows a partial section view of the exchange arm assembly along line 19—19 of FIG. 18;

FIGS. 23 to 26 show the slide load sequence; and

FIGS. 27 to 30 show the slide unload sequence.

DETAILED DESCRIPTION OF PREFERRED EMBODIMENTS

Figure 1:
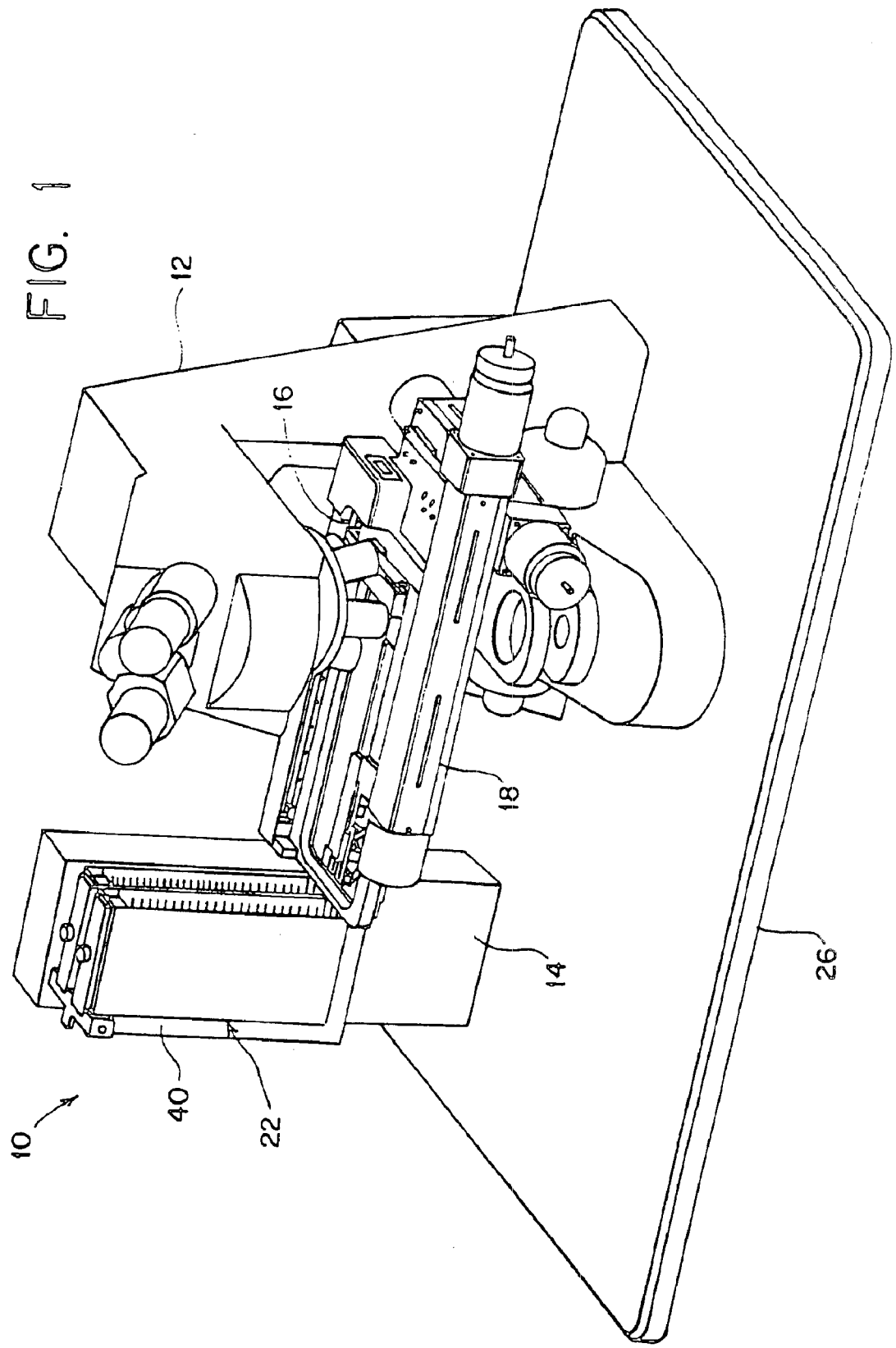
FIG. 1 shows a perspective view of the automated slide loader cassette instrument of the invention mounted to a microscope.

Turning now in detail to the drawings, FIG. 1 shows a perspective view of the automated slide loader cassette handler instrument 10 mounted to a microscope 12 comprising a slide cassette indexer 14 a slide exchange arm 16, and an XY-stage 18.

Figure 2:
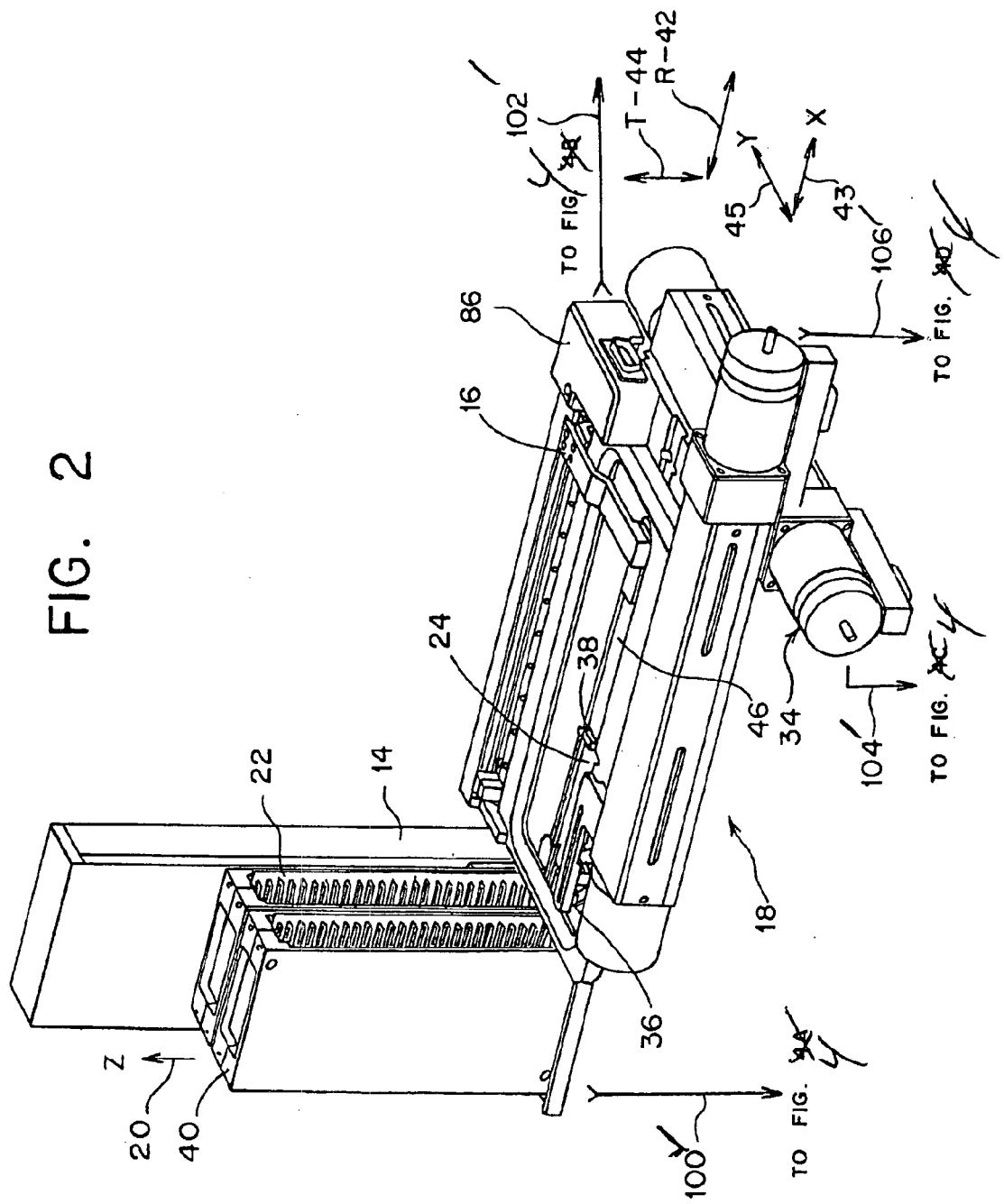
FIG. 2 shows the slide handler of the invention dismounted from a microscope.
Figure 5:
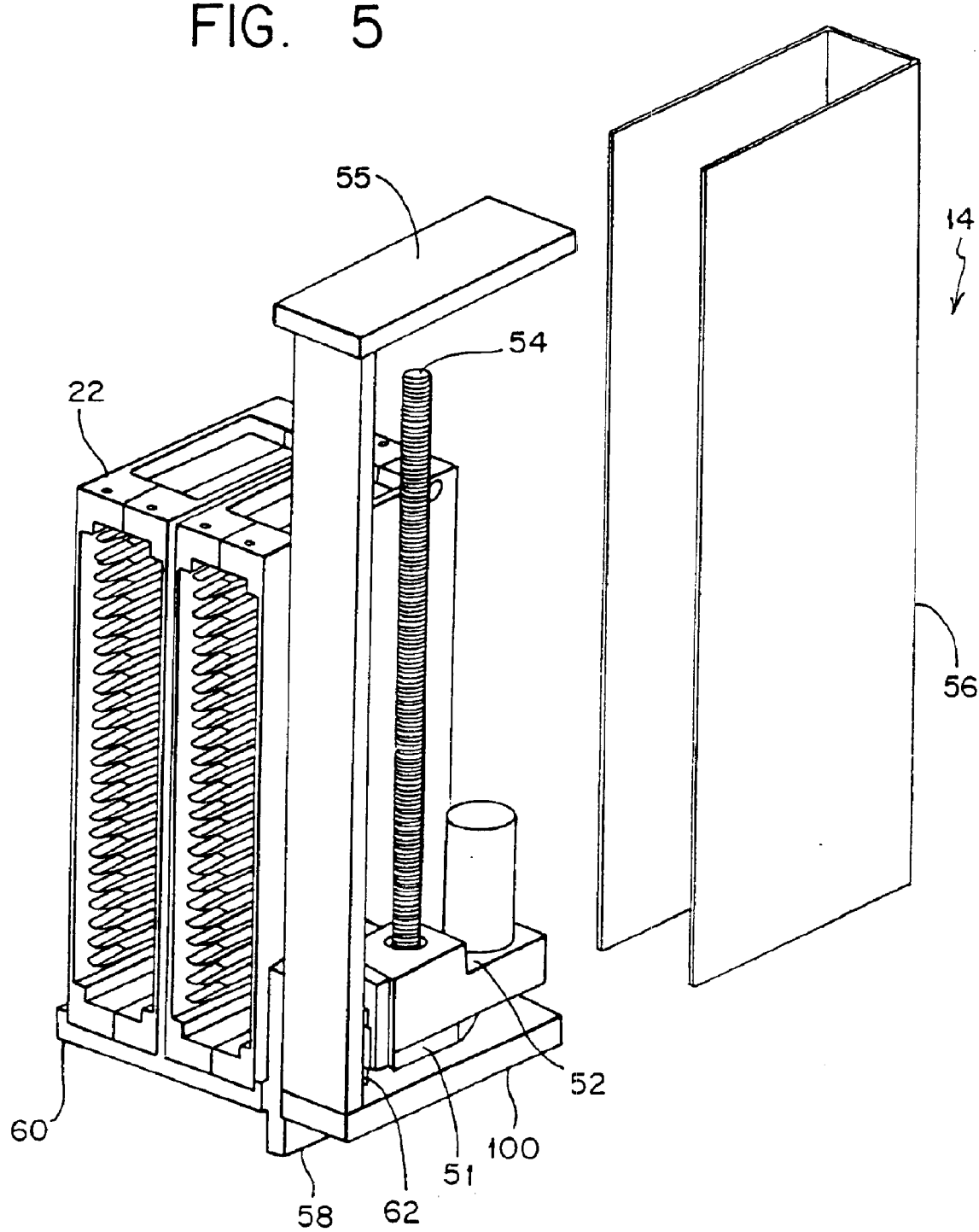
FIG. 5 shows the slide handler cassette indexer assembly.

As shown in FIG. 2 and in FIG. 5, the slide cassette indexer 14 has a single vertical axis Z 20 along which is moved a pair of side by side slide cassettes 22 to a proper height for transfer of each slide 24. The indexer 14 is mounted onto a common, stable base-plate 26, shown in FIG. 1. This base-plate 26 supports the microscope 12 so that the orientation of the indexer 14 and microscope 12 remains fixed.

The indexer 14, the slide exchange arm 16, and the XY-stage 18 are shown in FIG. 2 to be connected together and are integrated into one unitary modular instrument on the base plate 26 as shown in FIG. 1. While assembled on the base plate 26, these three components can be moved from one microscope to another. Alternatively these three components can remain in position on the base plate 26 and one microscope 12 can be detached and removed from the base plate and then another microscope 12 can be brought into position and attached to the base plate 26.

The indexer 14 as shown in FIG. 5 is actuated by a lift drive motor 52 which turns leadscrew 54 and has electrical and mechanical limits 51 and 55 at either end of travel.

FIG. 5 shows in greater detail the slide handler cassette indexer assembly after removal of the cover 56. Connector plate 58 connects together the slide cassette 22 and the lift platform 60 to the electric drive motor 52 and leadscrew 54, and to linear bearing 62.

Figure 9:
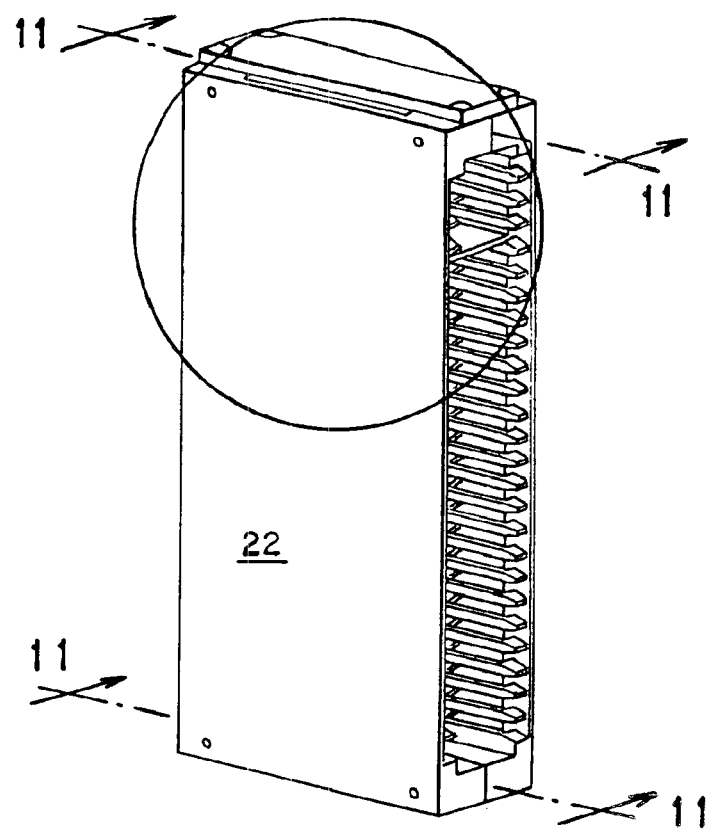
FIG. 9 shows another embodiment of the slide cassette.
Figure 10:
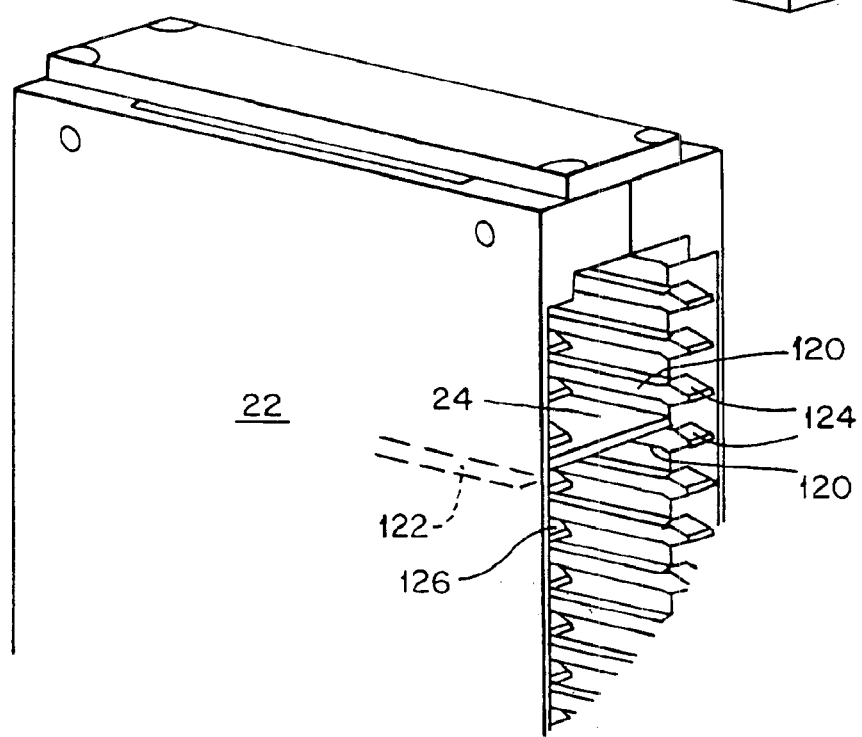
FIG. 10 shows an enlarged upper end of the slide cassette of FIG. 9.
Figure 11:
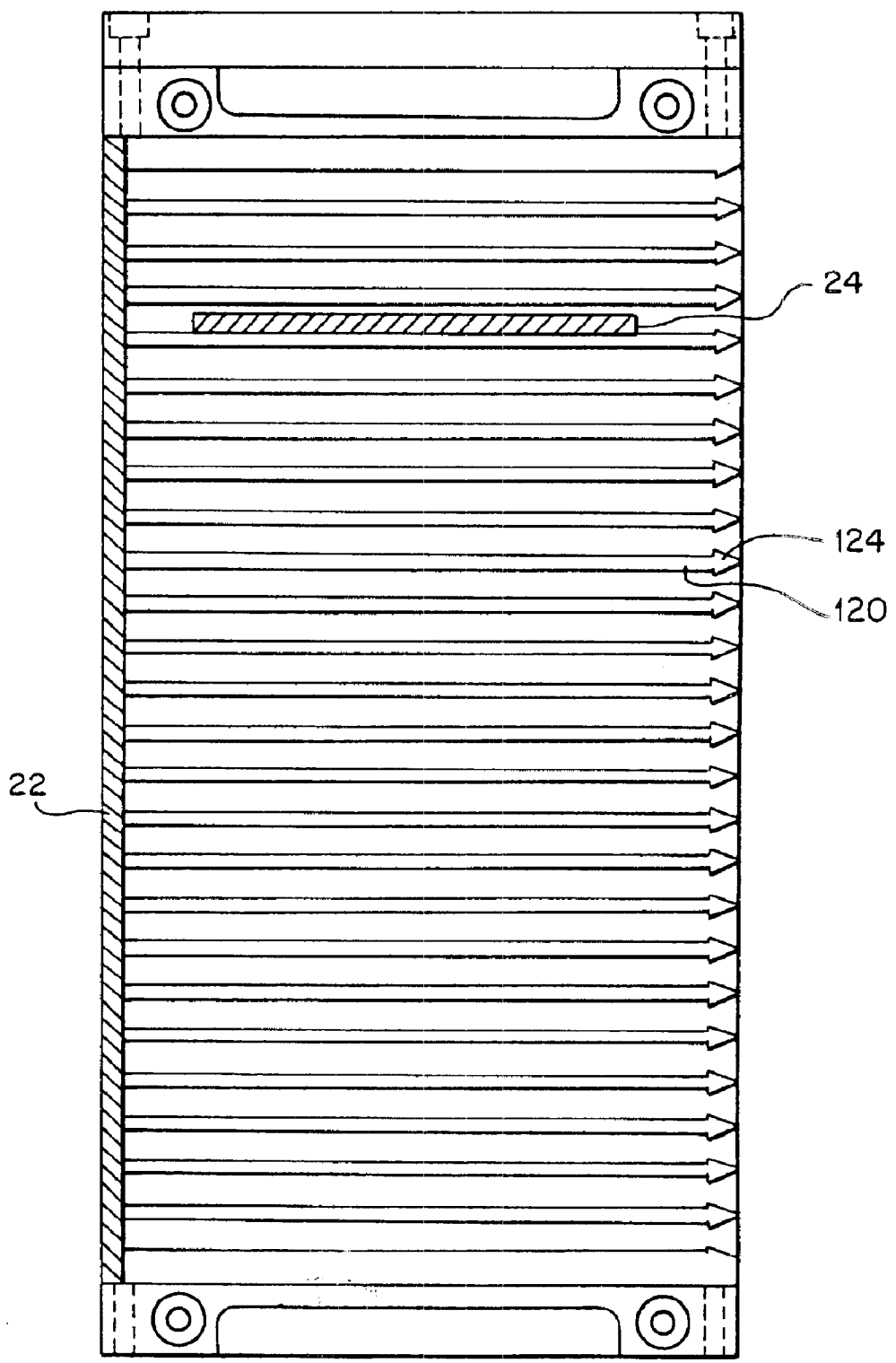
FIG. 11 shows a section view along line 11—11 of FIG. 9.

FIGS. 9, 10 and 11 show a further embodiment of the slide cassette 22. Here the slide 24 is supported by the two shelves 120 and 122. Shelf 120 has lip 124 while shelf 122 has lip 126. Each lip 124 and 126 prevents the slide from creeping out from the cassette either during transfer or by system vibration. The thickness of lip 126 or 124 is from 1.2 to 1.5 times greater than the thickness of shelf 122 or 120.

Figure 6:
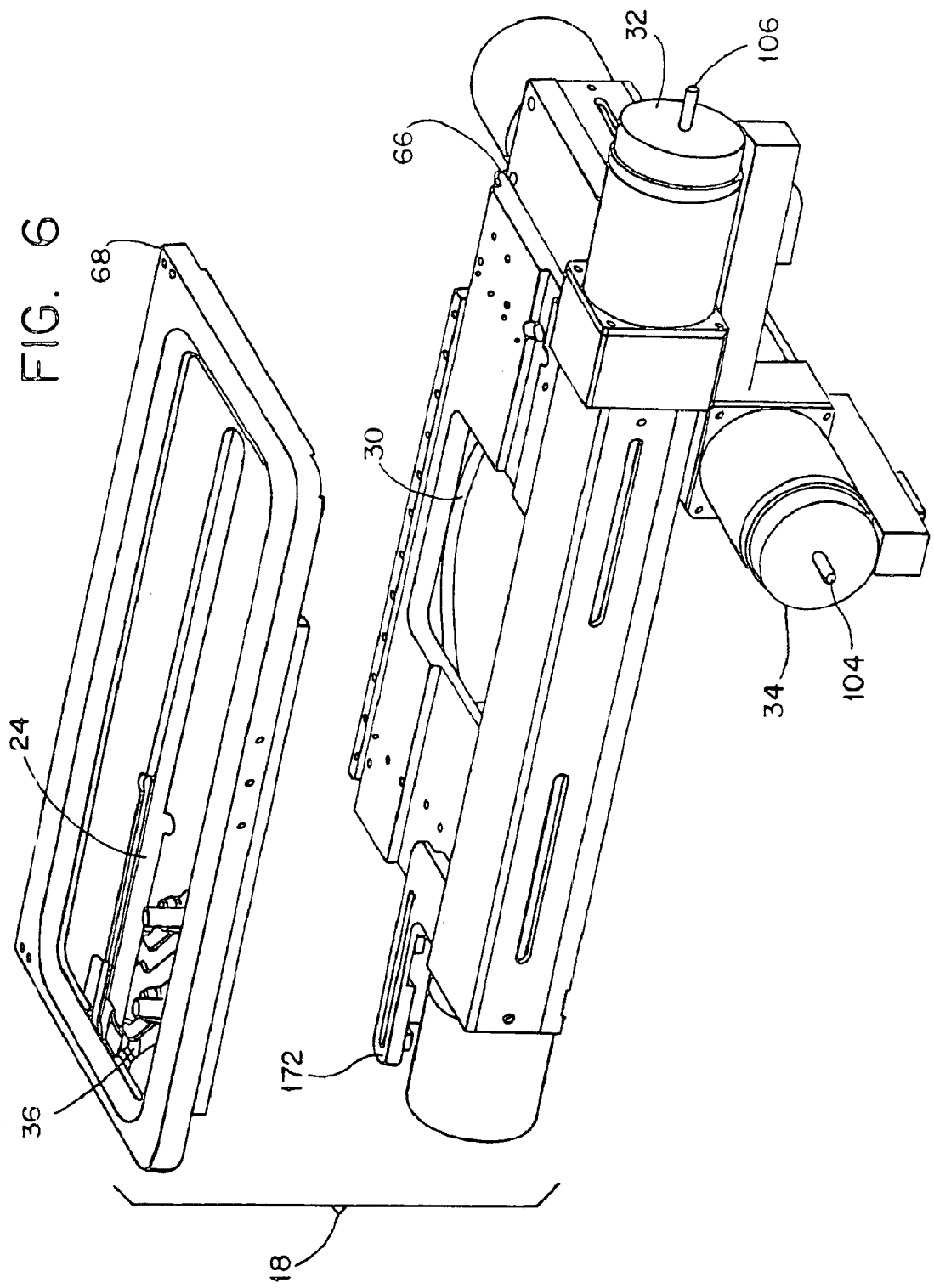
FIG. 6 shows the slide handler XY-stage partially assembled.

FIG. 2 and FIG. 6 show the XY-stage 18, with FIG. 6 showing an exploded view of the slide handler XY-stage assembly. The XY-stage 18 has attachment means outer ring 28 and inner ring 30 for mounting to the microscope 12 so that there is no interference with any optical operation of the microscope (See FIG. 1). The XY-stage 18 is driven in an X-axis 43 direction by X-axis electric drive motor means 32 and is driven in a Y-axis 45 direction by Y-axis electric drive motor means 34 by a leadscrew. The XY-stage has an integrated, spring loaded slide retention lever device 36 that locates a slide 24 and holds slide 24 in a fixed position. This retention lever device 36 is actively disengageable by mechanical linkage shown in FIGS. 21 and 22 when the XY-stage 18 moves to a slide exchange position.

Figure 8:
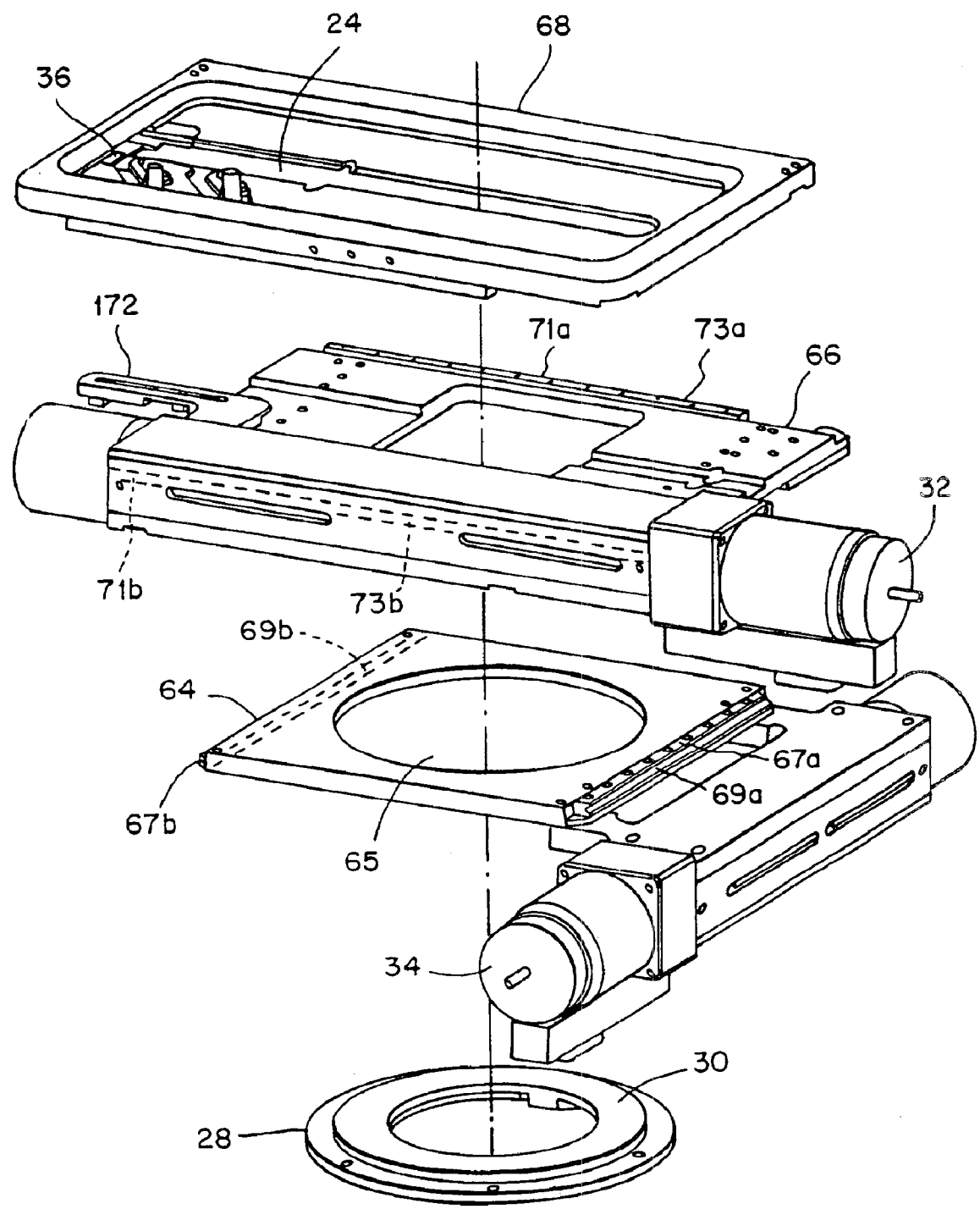
FIG. 8 shows an exploded view of the XY-stage.

FIG. 8 shows that the XY-stage includes an outer ring 28 attached to an inner ring 30, a bottom plate 64, a mid plate 66, and a top plate 68. Inner ring 30 is held by a friction fit within opening 65 of bottom plate 64 to which is attached motor 34. Mid plate 66 has motor 32 attached thereto.

Bottom plate 64 has linear bearings 67a and 67b attached thereto. Bearings 67a and 67b each comprises ball bearings in a V-groove raceway 69a and 69b respectively on opposite parallel sides thereof of bottom plate 64.

Mid plate 66 has linear bearings 71a and 71b attached thereto. Bearings 71a and 71b each comprises ball bearings in a V-groove raceway 73a and 73b respectively on opposite parallel sides thereof of mid plate 66. Each of linear bearings 67a, 67b, 71a and 71b are of the same shape as shown for V-groove 69a.

The attachment means 28 and 30 can also include a clip temporary attachment fastener or an adjustable vise type of temporary attachment fastener. Because the attaching by means 28 and 30 provides only temporary attachment, the handler instrument of the invention can be fastened to one microscope, and then readily detached and moved to another microscope. It can then be temporarily attached to the next microscope.

Figure 12:
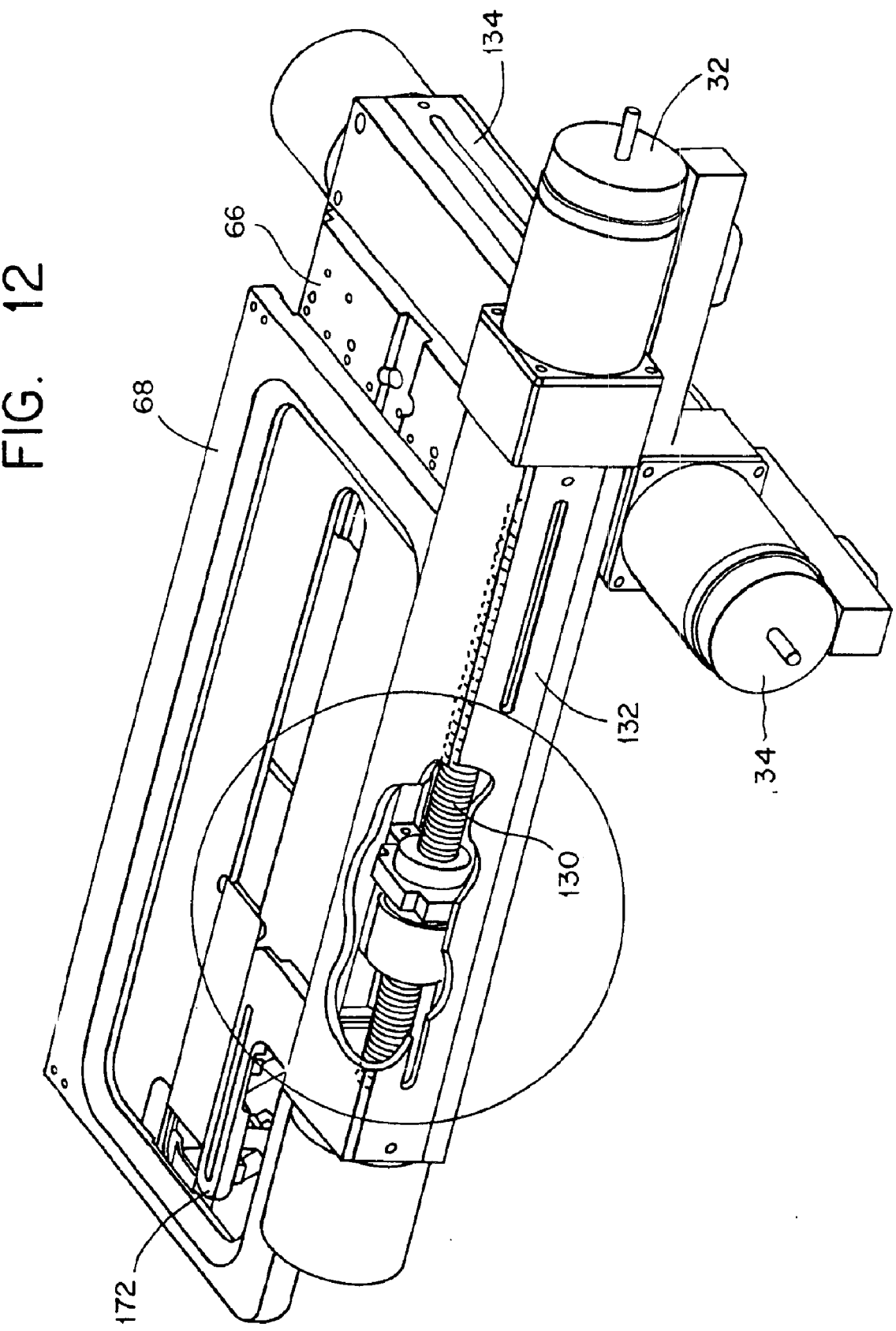
FIG. 12 shows a partial cut away view of the leadscrew housing of the XY-stage.
Figure 13:
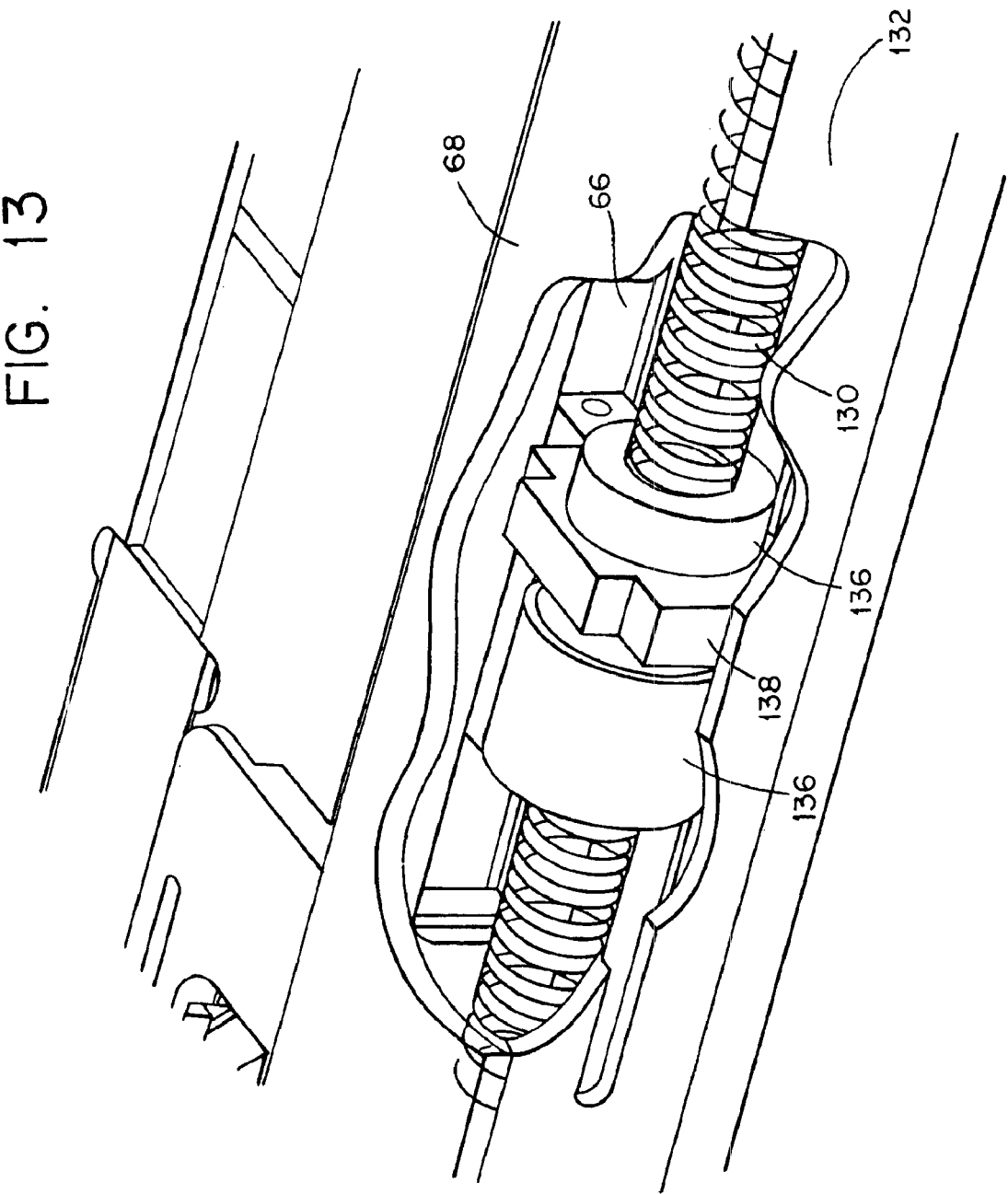
FIG. 13 shows an enlarged view of the cut away leadscrew housing of FIG. 12.

FIGS. 12 and 13 show how the XY-stage translation along the X-axis would occur by means of X-axis leadscrew 130, which is within X-axis leadscrew housing 132. The Y-axis housing 134 contains a Y-axis leadscrew (not shown) which operates analogously to the X-axis leadscrew 130. Leadscrew nut 136 fits around nut clamp 138, which clamp is connected to upper plate 68. Thus rotational movement of motor 32 causes rotational movement of leadscrew 130 which causes rectilinear movement of nut clamp 138 and linear movement of upper plate 68 which rests upon mid intermediate plate 66. The base plate 64 is mounted onto the microscope and is stationary.

Movement of the top plate 68 is guided by linear bearings 71a and 71b shown in FIG. 8, such that only movement in the X-axis direction is permitted.

Movement in the Y-direction is by motor 34 which causes the intermediate plate 66 to move, which is connected to the top plate which then moves in the Y-direction. The Y-axis leadscrew (not shown) is in housing 134 and is mounted onto the base plate 64 which is mounted onto inner ring 30. The Y-axis leadscrew has a screw nut and nut clamp which are connected to the intermediate plate 66 and move the intermediate plate 66.

Movement of the mid plate 66 is guided by linear bearings 67a and 67b shown in FIG. 8, such that only movement in the Y-axis direction is permitted.

The cassettes are made from molded plastic. The leadscrews and bearings are made from stainless steel. The other parts are made of anodized aluminum.

Figure 3:
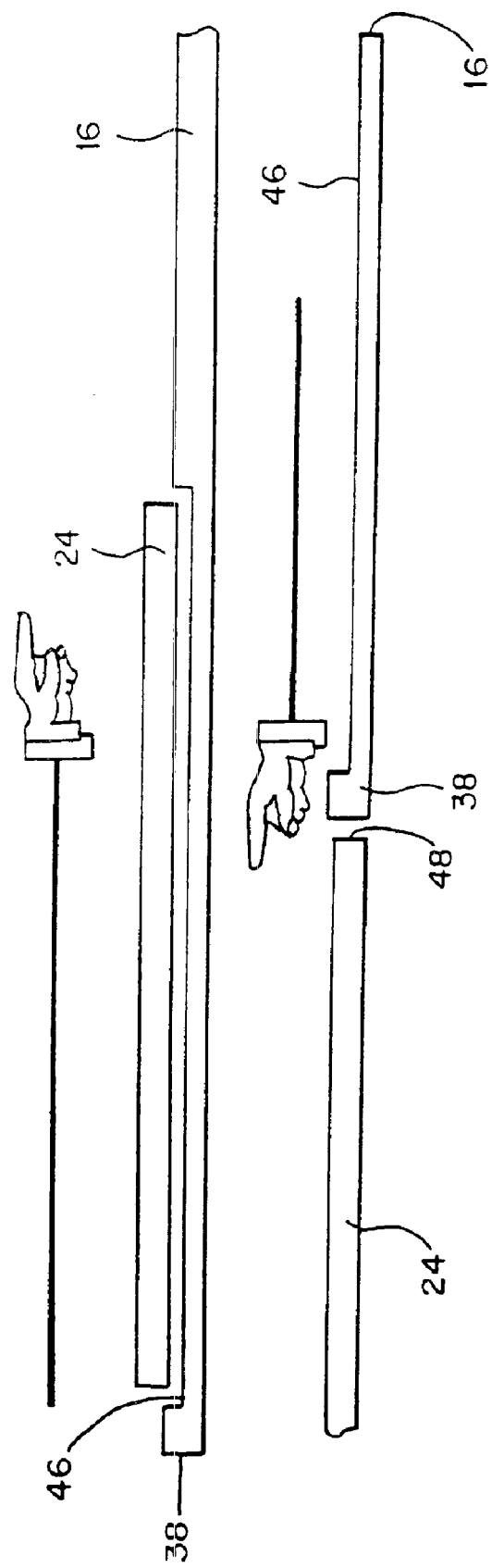
FIG. 3 shows the slide exchange arm of the invention.
Figure 7:
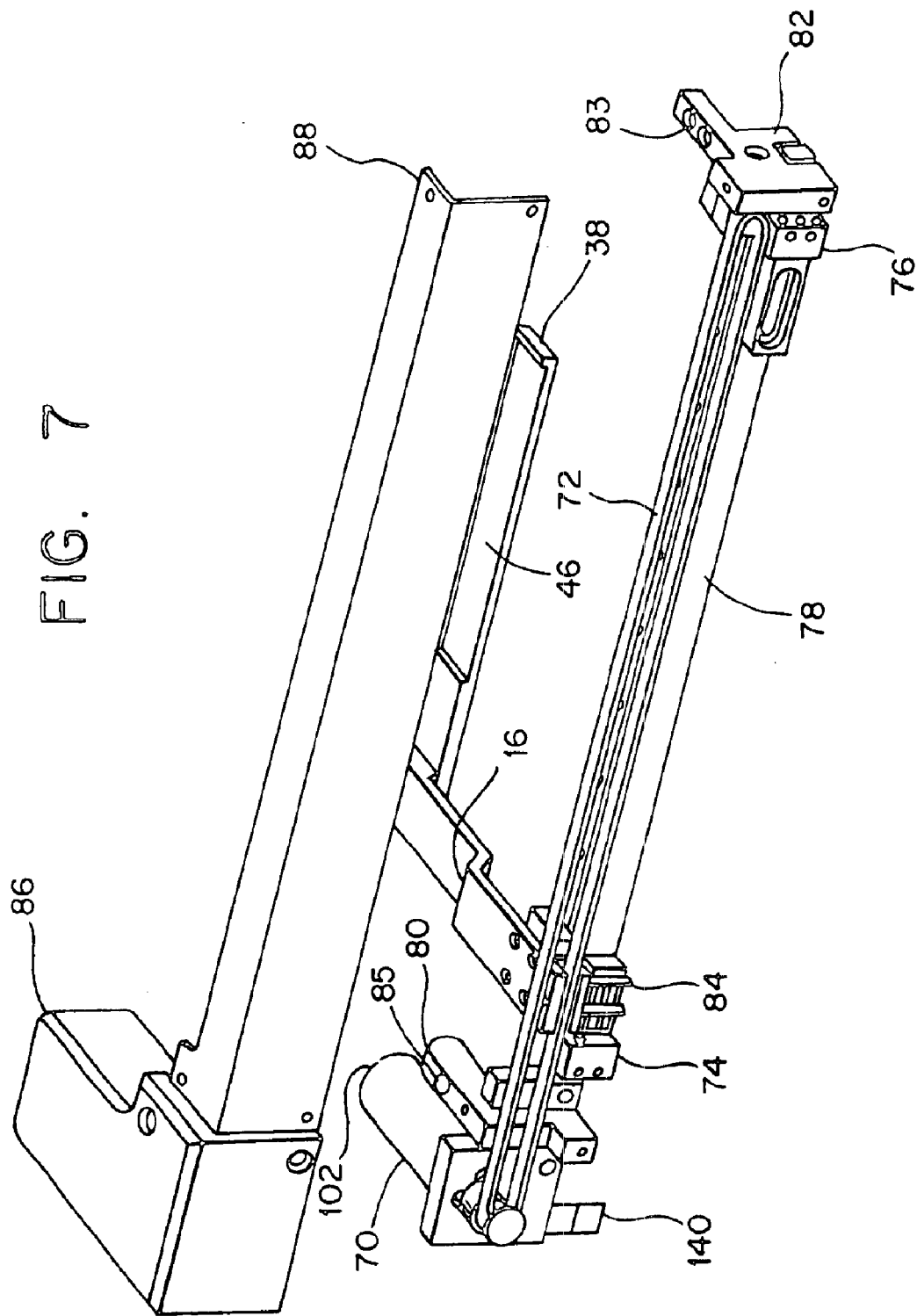
FIG. 7 shows the slide handler exchange arm assembly.

As shown in FIG. 2, the slide exchange arm 16 is mounted to the XY-stage 18. FIG. 3 shows that arm 16 has a distal finger 38 at the end of the arm that manipulates the slide 24 from the cassette retainer 40 to a proper position on the XY-stage 18 and subsequently back to the cassette retainer 40. FIG. 7 shows the slide handler exchange arm assembly in an exploded view.

The slide exchange arm 16 has a long travel axis 42 that is parallel to the X-axis 43 of the XY-stage. This long travel axis 42 is defined as the radius R-axis. The slide exchange arm has a short lift travel axis 44 that allows it to completely disengage the slide; and this lift travel axis 44 is the T-axis or tilt axis. The T-axis has two defined positions which are engaged and disengaged.

"Engaged position" means that the slide exchange arm is in same plane as is the slide. "Disengaged position" means that any movement of the slide exchange arm in the R-axis direction will not contact the slide.

As shown in FIG. 7, the arm 16 is driven in the R-axis direction by an electric motor 70 which drives continuous belt 72 with end-limits 74 and 76. End limits 74 and 76 are electrical safety switches that inform the controller that the limit of travel is reached for the arm 16. The electronic controller stops the motor 70. The T-axis (or tilt axis) movement is actuated by mechanical linkage to coordinated motion from the XY-stage X-axis. Linear bracket 78 connects together end-limits 74 and 76, and supports motor 70. Bearing support 82 supports linear bracket 78 and end-limit 76. End-limit trigger spring 84 acts as a shock absorber to dampen impact due to travel. Motor cover 86 is fits above and around motor 70 and is connected to drive mechanism cover 88 which fits above belt 72.

Figure 14:
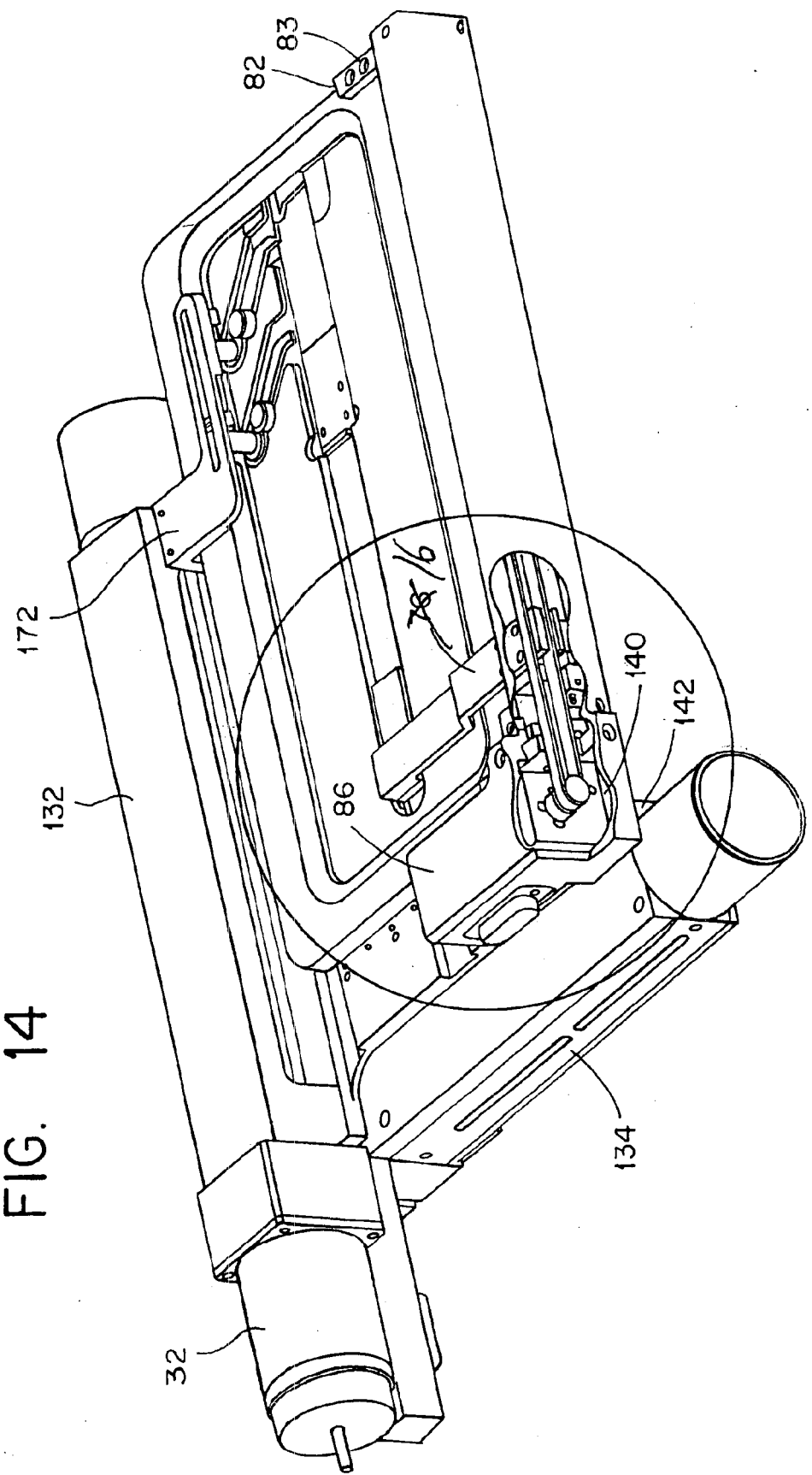
FIG. 14 shows the XY-stage and the slide exchange arm assemblies in combination.
Figure 15:
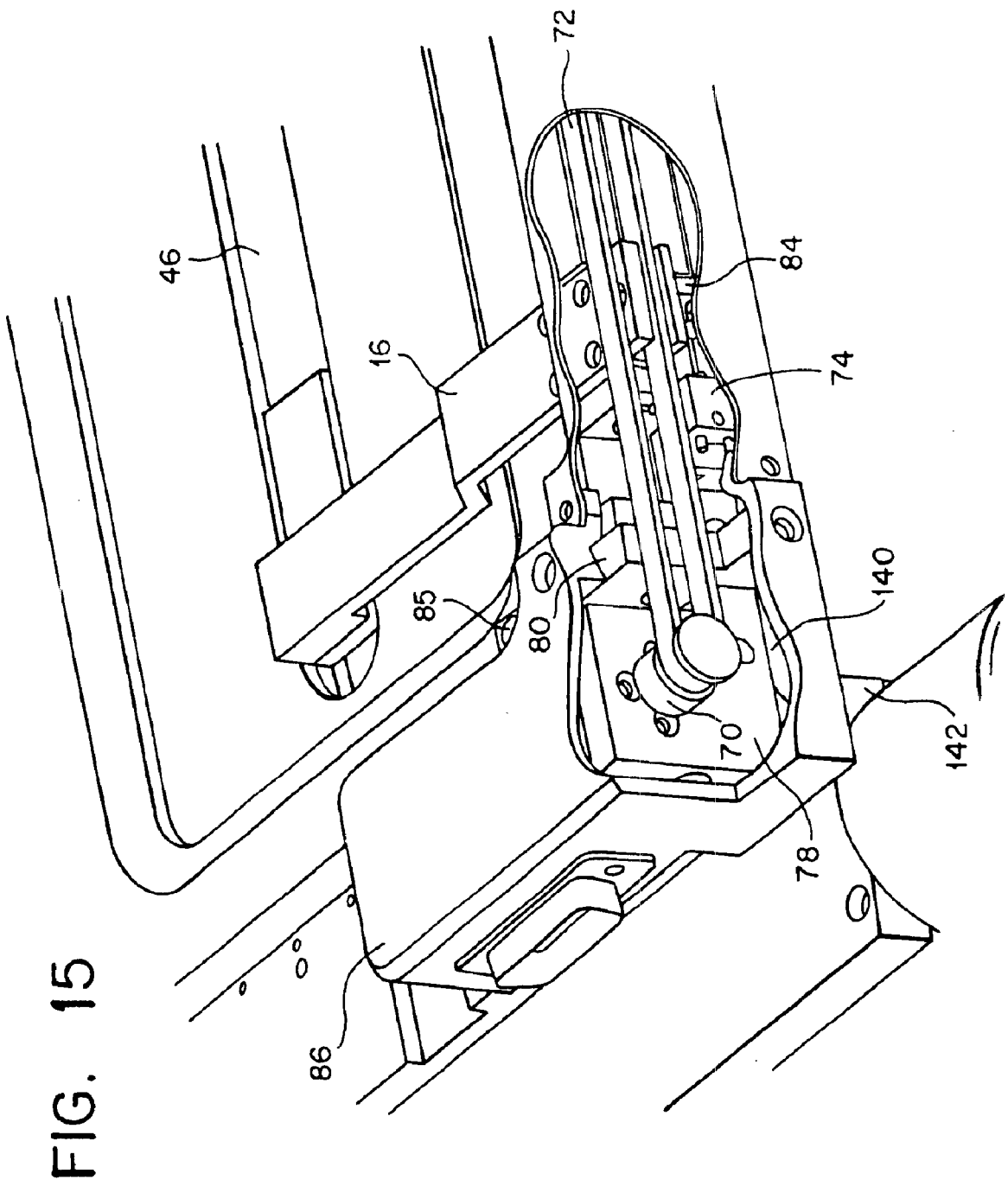
FIG. 15 shows an enlarged partial cut away view of the XY-stage with slide exchange arm of FIG. 14.

The slide exchange arm mechanism is explained, first with regard to the R-axis or the radius axis. The exchange arm assembly is illustrated in FIGS. 7, 14 and 15. The mechanism includes the covers 86 and 88 which are removed in FIG. 7. The covers are not an integral part of the operation of the exchange arm. The support beam 78 runs the full length of the mechanism and serves to tie all the components together. The motor 70 is attached to one end. A linear ball bearing 84 supports the travel of the arm 16 and distal finger 38. Electrical end limits 76 and 74 are also attached to the beam 78. The support beam 78 is attached at two pivot points to blocks 80 and 82. Each attached pivot point includes a bushing and an axle. Attachment screws connect the arm assembly to the top plate 68 through openings 83 in block 82 and openings 85 in block 80.

In operation, the motor shaft rotates, moving the continuous belt 72. The arm 16 is clamped to the belt 72 so as the motor turns, the arm 16 travels on the linear bearing 84. The motion limits are defined by the electrical end limits 76 and 74.

With regard to the T axis, or tilt axis, the slide exchange arm operates as shown in FIGS. 16, 17, 18 and 19. The components of the T-axis motion include the R-axis assembly mounted on pivots, an actuator bearing 140, and an actuator trigger block 142. Bearing 140 and block 142 provide a mechanical linkage to coordinated motion from the XY-stage X-axis for T-axis movement of the slide exchange arm.

The T-axis or tilt axis motion can be seen by comparing FIGS. 16 and 17 with FIGS. 18 and 19. The T-axis motion is achieved by tilting the support beam 78 with the tilt shown in FIGS. 18 and 19. The beam tilts about the pivot axis defined by the mounting bushing fixed in the blocks 80 and 82. The normal T-axis state (engaged, un-actuated) is spring loaded and is shown in FIGS. 16 and 17. To move the T-axis to the disengaged state, the X-axis of the stage is moved such that the actuator trigger block 142 contacts and presses against the actuator bearing 140 that is fixed to the support beam 78. An outward force causes the support beam 78 to tilt through an angle θ and thereby lowering the exchange arm 16 to the disengaged position through the same angle θ, as shown in FIG. 19. Thus pocket 46 and finger 38 are below and not contacting the slide 24. The angle θ can range between 2 to 10 degrees, preferably between 4 to 6 degrees.

The actuator trigger block 142 is attached to the Y axis of the XY-stage. As the XY stage is moved along the X-axis, and when the actuator bearing 140 contacts the actuator trigger block, the exchange arm assembly is then tilted. This causes the end 38 of the exchange arm to be tilted beneath the bottom of the slide enabling the exchange arm to move clear under the slide.

Figure 20:
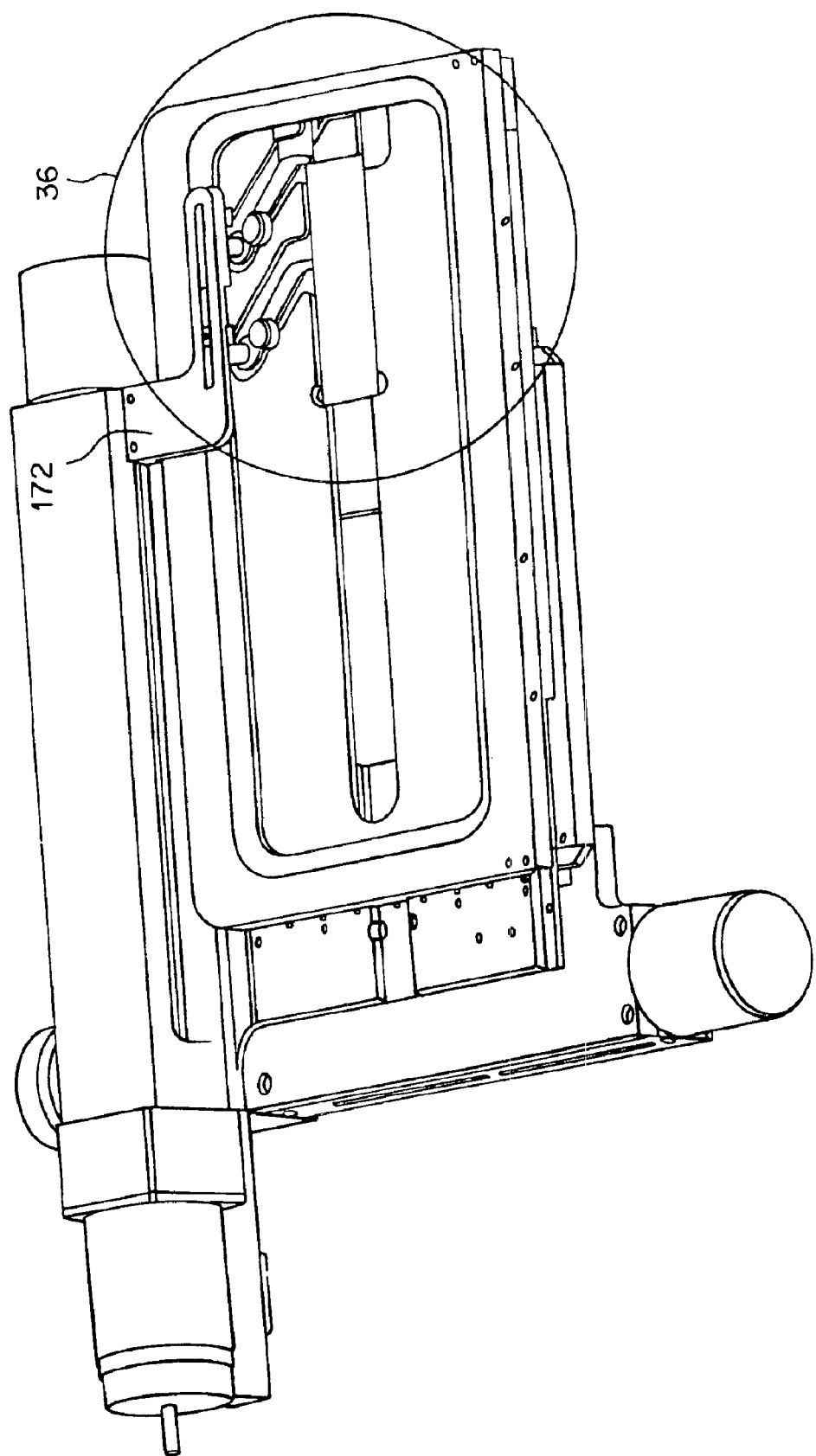
FIG. 20 shows a perspective view of the XY-stage and the slide holder fingers.
Figure 21:
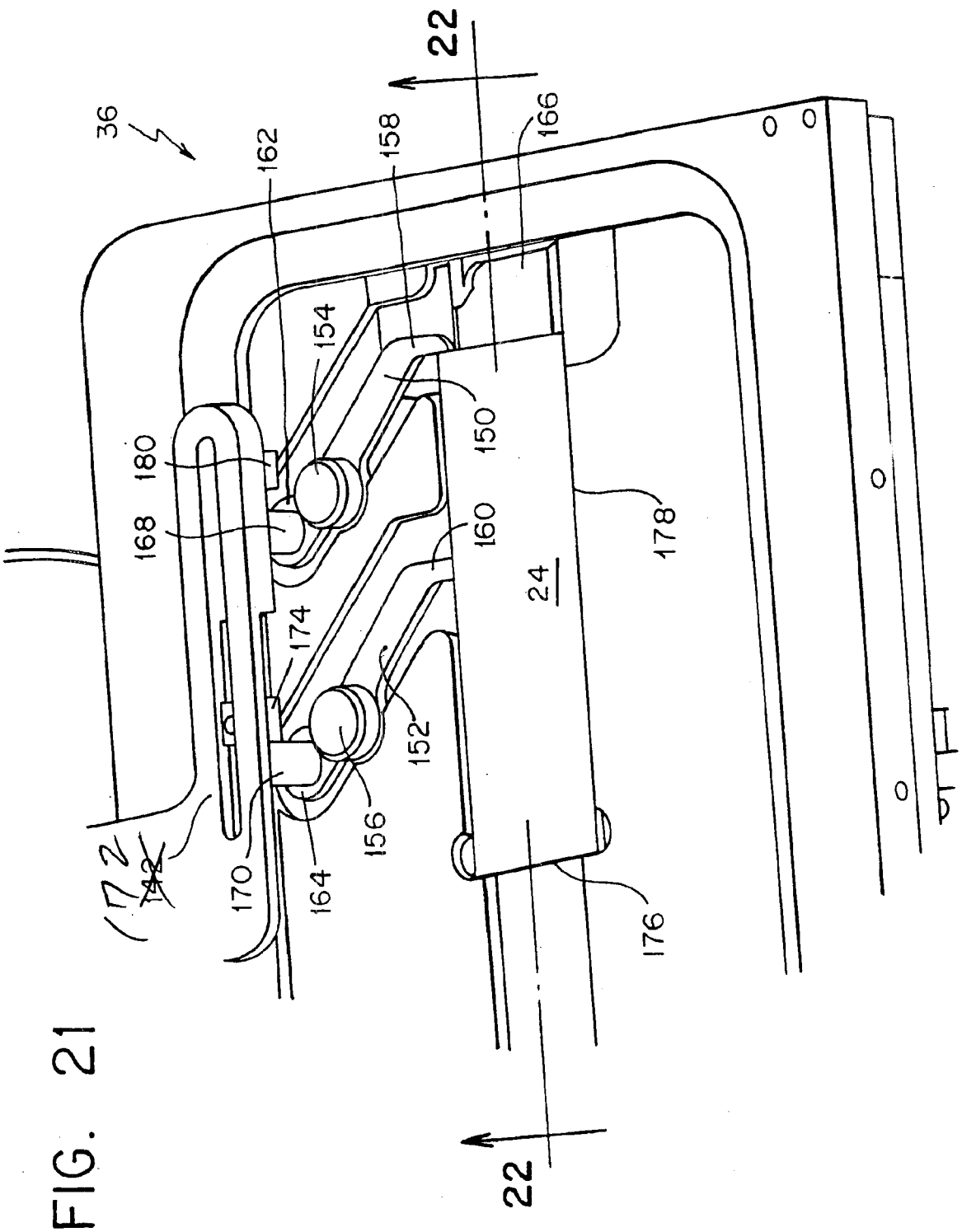
FIG. 21 shows an enlarged view of the slide holder assembly of FIG. 20.
Figure 22:
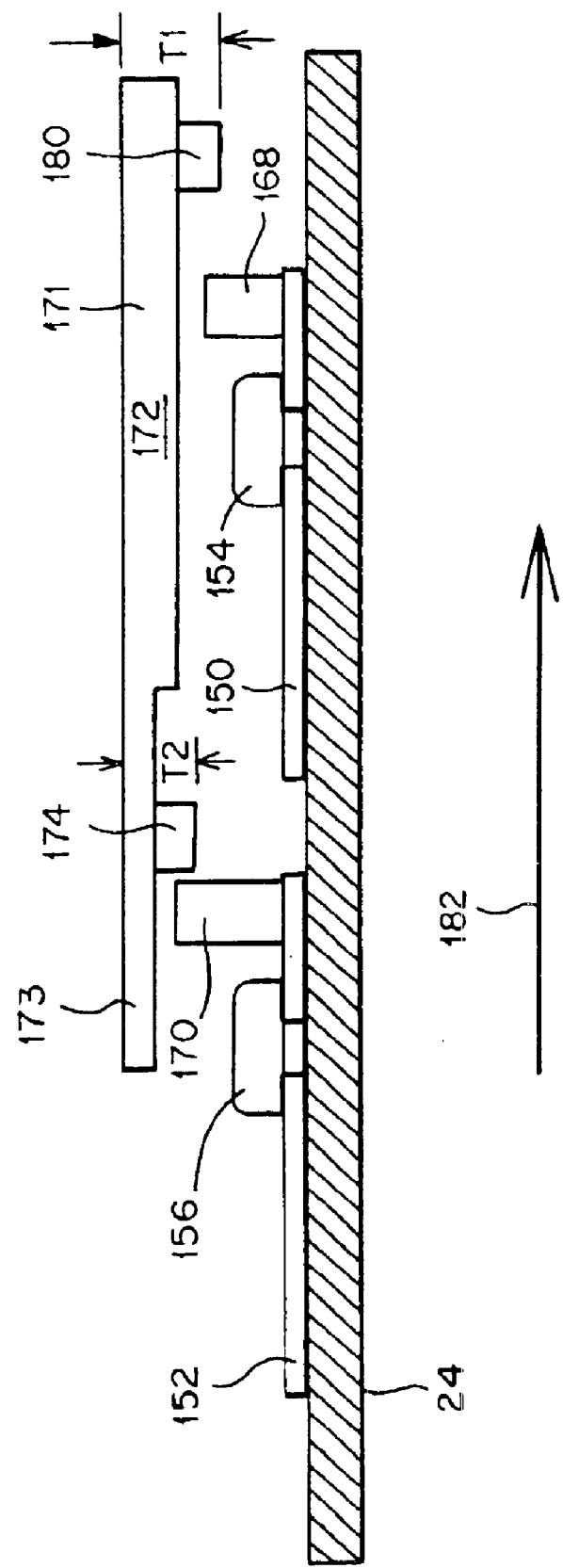
FIG. 22 shows a section view along line 22—22 of FIG. 21 for the slide finger actuation mechanism.

The slide holder retention device assembly 36 is shown in FIGS. 20, 21 and 22. The slide holder assembly 36 of the invention is a component that enables the slide to be placed firmly, reliably and accurately on the XY-stage. The elements of the slide holder retention device assembly include two spring loaded fingers, the actuator means and the recess in which the slide is held. The spring loaded fingers and the actuator means provide a mechanical linkage to engage the slide or to disengage the slide whenever the XY-stage moves along the X-axis.

The two spring loaded fingers 150 and 152 separately hold the slide 24 from two slides forming one corner of the slide by pressing against the conjugate sides of the slide. Each finger is constructed as a lever rotating about spring loaded pivot 154 or spring loaded pivot 156 respectively between the contact end 158 of finger 150 and contact end 160 of finger 152 and the actuation end 162 of finger 150 and actuation end 164 of finger 152. The contact end 158 or the contact end 160 of the finger that contacts the slide is shaped in such a way as to facilitate its function. To effectively hold the slide from the slide end, the first finger 150 has hook shaped end 158 to wrap around the corner of the slide to provide force along the XY-stage X-axis. The second finger 152 is shaped to provide force against the slide along the XY-stage Y-axis. The second finger 152 may also have a downward facing bevel to hold the slide down flat in the recess 166 on the XY-stage. On the actuation end of each finger there is a post 168 on finger 150 and post 170 on finger 152 to engage the actuator 172. The finger post 168 on finger 150 is shortened so that it can pass clearly below and not contact the actuator stop block 174 for finger 152. Conversely actuator post 170 for finger 152 is taller than post 168. (See FIG. 22).

The recess 166 of the XY-stage that forms the confines for the slide is designed with an open end so that the slide can be manipulated in the approximate locating position by the exchange arm. The width of the recess 166 is determined such that the slide 24 is guided by the walls of the recess should it become upset during the transfer process. Two of the walls 176 and 178 of the recess serve as fixed alignment stops for the slide to rest against after the fingers are activated. The wall 178 along the X-axis features an inverted bevel, that is wider at the bottom than the top, that will force the slide 24 to be held tightly against the bottom of the recess. The recess is coated with a low friction high durability coating that facilitates the slide handling and has a long lifetime against the scratching of the hard, sharp glass slides.

The actuator 172 provides the means to actively release the slide fingers from engagement. Since the fingers 150 and 152 are spring loaded to hold the slide in place, the actuator 172 must act against the springs to release the slide. Pivot 154 contains a spring and pivot 156 contains a spring. The actuator 172 is fixed to the middle plate 66 of the XY-stage. This makes the actuator stationary with respect to the X axis while allowing it to move with the Y-axis of the XY-stage. The actuator 172 has two fixed stop blocks 174 and 180 that contact the posts 170 and 168 respectively on each finger. The design is such that the actuator stop block 174 is high enough that the finger 150 can pass beneath block 174 without contacting block 174, while finger 152 will contact the block 174 and actively release the tension on the finger. The post 168 on finger 150 will contact the actuator stop block 180. The post 170 on finger 152 will contact the actuator stop block 174.

These differences in height are shown in FIG. 22, which provides a cross-section of the slide finger actuation mechanism for the integrated spring loaded slide retention lever device 36. The arrow 182 indicates the direction of movement of the XY-stage as it moves to the slide load position. Actuator 172 has thicker end 171 to which block 180 is attached and has narrower end 173 to which block 174 is attached. Blocks 174 and 180 are of the same thickness. Thus the total distance of 171 plus 180 or T1 is greater than the total distance of 173 plus 174 or T2. This shorter distance T2 enables post 168 to pass beneath block 174.

The slide load operation into retention device 36 is explained as follows. Once the exchange arm manipulates the slide to the approximate location and retracts to the clear position, the XY-stage X-axis moves the actuator 172 to engage the fingers 150 and 152. The fingers 150 and 152 are engaged in sequence. As the XY-stage moves, finger 150 is engaged first. This provides that the slide is forced against the end wall 176. This orientation is performed first because the force that finger 152 applies against the long edge 178 would not allow the finger 150 to complete the alignment by pushing the slide against the wall 176. Shortly thereafter the second finger 152 is engaged to fully align and ensure that the slide is held in place.

The slide load operation is shown in greater detail in FIGS. 23, 24, 26 and 26 in this sequence. FIG. 23 shows in the first part of the load sequence that the slide 24 has already been pulled from the cassette. Both slide alignment fingers 150 and 152 are disengaged. The slide exchange arm will have previously pulled the slide 24 from the cassette and will have deposited the slide on the XY-stage at the approximately correct and aligned position.

FIG. 24 shows the second part of the slide load sequencing. Here movement of the actuator 172 to the left occurs as the XY-stage moves along the X-axis to the left in the direction of arrow 184. The XY-stage moves to about 4 mm away from the cassette. Post 168 on finger 150 no longer contacts stop block 180, so that the first finger 150 can be spring rotated around pivot 154 and engage slide 24 at slide end 186.

FIG. 25 shows the third part of the slide loading sequencing. Here further movement of the actuator 172 to the left occurs as the XY-stage moves along the X-axis to the left. Post 170 on finger 152 no longer contacts stop block 174, so that the second finger 152 can be spring rotated around pivot 156 and engage slide 24 at the side edge 188 of the slide.

FIG. 26 shows the fourth part of the slide loading sequencing. Here further movement of the actuator 172 to the left has occurred as the XY-stage moves along the X-axis to the left. Actuator 172 is free and clear of the two fingers 150 and 152. Finger 150 presses against the end 186 of the slide, and finger 152 presses against the side edge 188 of the slide. Each finger is spring loaded and holds the slide in place.

The slide unload operation from retention device 36 is explained as follows. When the XY-stage moves to the programmed unload position, the fingers are released. Finger 152 is released first followed by finger 150. The release order is the opposite of the sequence that is performed for the load operation.

The slide unload operation is shown in greater detail in FIGS. 27, 28, 29 and 30 in this sequence. FIG. 27 shows the first part of the unload sequence. Here the first finger 150 engages and presses against the end 186 of the slide 24 while the second finger 152 engages and presses against the slide edge 188 of the slide. These two fingers are held in place by the spring loaded pivots, namely pivot 154 for finger 150 and pivot 156 for finger 152.

FIG. 28 shows the second part of the unload sequence. Here the actuator 172 moves to the right in the direction of arrow 190. The slide holding fingers are still contacting the slide, but are in position to be disengaged. The actuator 172 is moved to the right as the XY-stage moves along the X-axis to the right. The actuator 172 has the two stop blocks 174 and 180 which have not yet contacted each respective finger post 170 or 168 respectively. Thus the two fingers 150 and 152 do not move at this point, and the slide is still held in place.

FIG. 29 shows the third part of the unload sequence. Here the XY-stage moves along the X-axis to the right approximately 4 mm. This moves the actuator 172 attached to the XY-stage to the right also about 4 mm, such that the actuator stop block 174 contacts finger post 170 on finger 152. This causes finger 152 to rotate around spring loaded pivot point 156 and to move away from edge 188 of slide 24. However finger 150 is still contacting slide 24 at end 186 due to spring loaded pivot 154.

FIG. 30 shows the fourth part of the unload sequence. Here the XY-stage moves further to the right, so that the actuator 172 attached to the XY-stage also moves further to the right as indicated by arrow 190. Thus the actuator stop block 180 contacts finger post 168 on finger 150. This causes finger 150 to rotate around pivot point 154 and move away from end 186 of the slide 24. Thus the slide is capable of being moved by the slide exchange arm, since the two fingers have been released and no longer contact the slide.

The method of operation for the slide handler instrument of the invention is as follows. The slide handler XY-stage 18 transfers slides 24 because the instrument is coordinating 5 axes of motion: the XY-stage X-axis, the XY-stage Y-axis, the cassette indexer Z-axis, the slide exchange arm R-axis and the slide exchange arm T-axis. While the slide retrieve and replace operations utilize the same slide exchange arm 16 and finger 38, the sequences are different.

Figure 4:
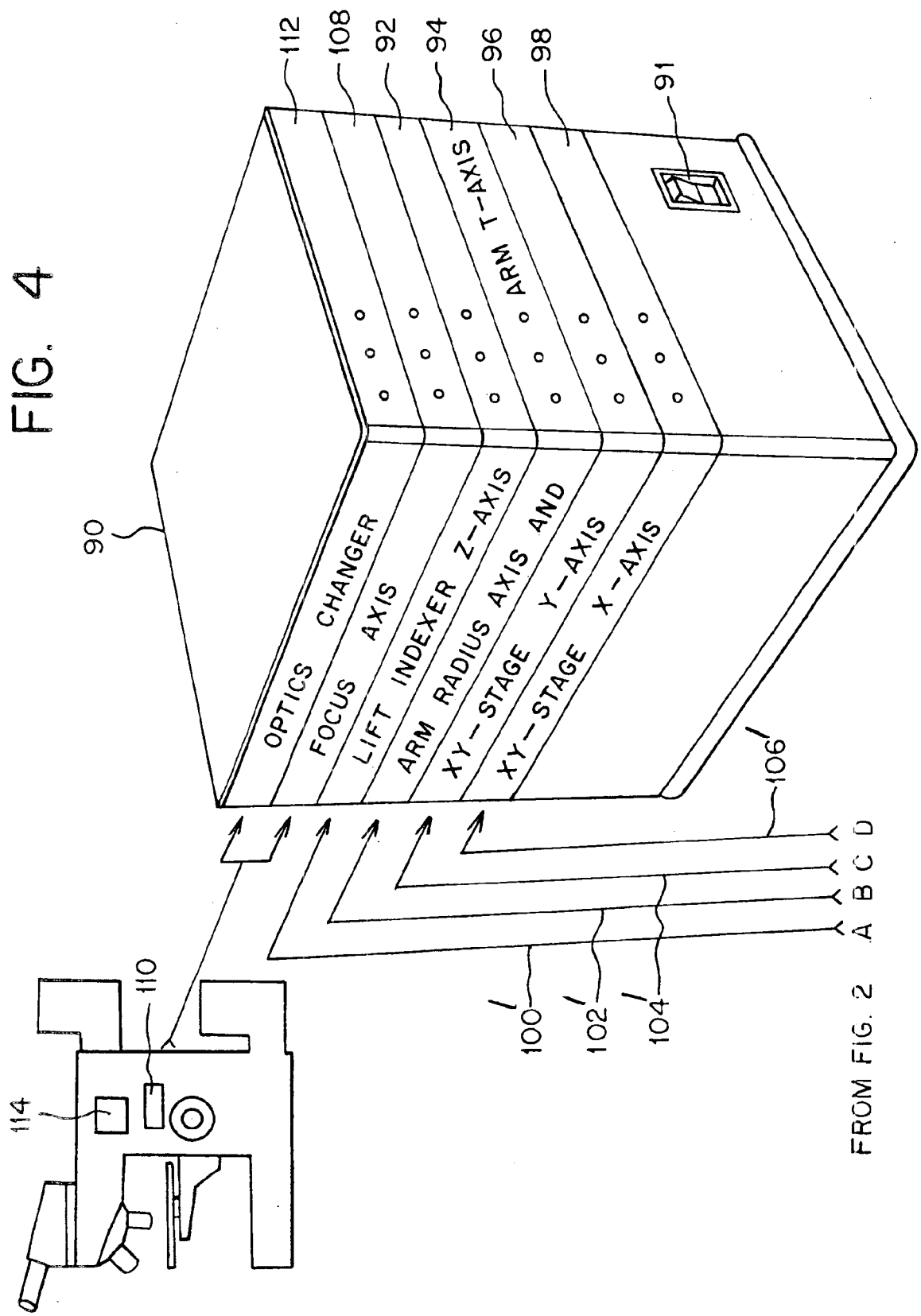
FIG. 4 shows an electronic controller for the invention.

The vertically assembled electronic controller system 90 is shown in FIG. 4 and provides high-level commands for slide transfer. Controller 90 would be plugged into a conventional power source such as a wall outlet for 110 volts A.C. Then the main power switch 91 would be turned to the on-position. This simplifies the application of a conventional computer program to control mechanical movements in FIG. 2. Controller 90 is made up of individual modular control unit 92 which controls the indexer Z-axis; and includes individual modular control unit 94 which controls the arm R-axis and T-axis; individual modular control unit 96 which controls the XY-stage Y-axis; and individual modular control unit 98 which controls the XY-stage X-axis.

In the procedure of the transfer process there are specific positions that define the path of movement along each axis. The following explanation defines sequences and the positions of the various moving components.

Modular control unit 92 sends an electrical command control signal over lead line 100' to electric motor 52 to either start it or to stop it and to control its direction of rotational movement. Modular control unit 94 sends an electrical command control signal over lead line 102' to electric motor 70 to either start it or to stop it and to control its direction of rotational movement. Modular control unit 96 sends an electrical command control signal over lead line 104' to electric motor 34, to either start it or to stop it and to control its direction of rotational movement. Modular control unit 98 sends an electrical command control signal over lead line 106' to electric motor 32 to either start it or to stop it and to control its direction of rotational movement.

In the fetch or retrieve cycle, the home position is the position where the arm 16 is clear of the microscope optics and in the engaged position and the XY-stage 18 is free to position the slide 24. In the XY load position, the XY-stage is at the XY position for moving arm 16 into the selected cassette 22 of cassette retainer 40. The axes used are the X-axis and Y-axis; and the appropriate commands are sent from modular controller unit 96 over lead 104' to drive motor 34 and are sent from modular controller unit 98 to drive motor means 32 over lead 106'. The drive motors 34 and 32 of the XY-stage move the arm 16 to a location which is near to and adjacent to the cassette retainer 40 but is outside of the retainer 40. Motor 70 moves the arm and finger 38 into and out of cassette retainer 40.

In the arm extend retrieve or fetch position, the slide exchange arm 16 is extended between slides 24 in the cassette retainer 40 to a position so that the slide 24 will engage the finger 38 of the slide exchange arm 16 when cassette indexer 14 is lowered. The axes used are the X-axis, Y-axis, R-axis, T-axis, and Z-axis. The appropriate commands are sent from modular controller 98, 96, 94 and 92 respectively, to electric motors 32, 34, 70 and 52 respectively.

When the slide 24 is placed in position on the finger 38, the cassette indexer 14 lowers by approximately 2 mm to place the slide 24 into the pocket 46 on the slide exchange arm finger 38. The axis used is the Z-axis; and the appropriate commands are sent from modular controller unit 92 to electric motor 52.

In the arm retract to slide position, the arm 16 retracts from the cassette retainer 40 carrying a slide 24. The retraction motion ends with the slide 24 in position on the viewing stage of microscope 12. The axis used is the R-axis; and the appropriate commands are sent from modular controller unit 94 over lead 102' to electric motor 70.

In the arm disengage position, the slide exchange arm 16 and finger 38 drop below the slide 24, leaving the slide 24 in position on the XY-stage. The axis used is the T-axis; and the appropriate commands are sent from modular controller unit 94 to electric motor 70.

In the arm clear position, the slide exchange arm 16 moves to the farthest position with the arm 16 in the disengaged position to be clear of all the microscope devices and to be clear of the slide 24. The axis used is the R-axis; and the appropriate commands are sent from modular controller unit 94, to electric motor 70.

In the arm engage position, to pick up the slide 24 the slide exchange arm 16 moves to the engaged position (return to home). The axis used is the T-axis; and the appropriate commands are sent from modular controller unit 94 to electric motor 70 over lead 102.

In the lock slide position, the XY-stage 18 moves away from the load position to cause the retention device to engage the slide 24. The axis used is the X-axis; and the appropriate commands are sent from modular controller unit 98 to motor 32 and from modular controller unit 96 to motor 34.

In the replace cycle, the home position is the position where the arm 16 is clear of the microscope optics and the XY-stage 18 is free to position the slide and specimen, and the T-axis is engaged. The axes used are the T-axis and the R-axis; and the appropriate commands are sent from modular controller unit 94 to electric motor 70.

In the slide contact position, the finger 38 of the arm 16 is contacting the leading edge 48 of the slide 24, as shown in FIG. 3. The axes used are the T-axis which is engaged and the R-axis; and the appropriate commands are sent from modular controller unit 94 to electric motor 70.

In the XY load position, the XY-stage 18 is at the XY position for loading the slide 24 into the selected cassette 22. The axes used are the X-axis and Y-axis; and the appropriate commands are sent from modular controller unit 98 and 96 to electric motors 32 and 34.

In the cassette index position, the cassette index 14 moves the cassette retainer 40 to a selected slot in the cassette 22. The axis used is the Z-axis; and the appropriate commands are sent from modular controller unit 92 to electric motor 52.

In the arm extend replace position, the arm 16 is contacting the leading edge 48 of the slide 24 so that the slide is pushed and is therefore fully inserted into the cassette 22. The axis used are as follows, namely T-axis (engaged), R-axis, X-axis and Y-axis, and the Z-axis. The appropriate commands are sent from modular controller unit 94, 98, 96 and 92 to electric motors 70, 32, 34 and 52 respectively.

In the arm retract position, the arm 16 is at a position that is clear of the cassette 22 for proper indexing. The axis used is the R-axis; and the appropriate commands are sent from modular controller unit 94 to electric motor 70 over lead 102.

In both transfer modes, the XY-stage 18 and the cassette indexer 14 move to the specified positions. The XY-stage moves in the X-axis and the Y-axis to the load position for the specified cassette 22. The programmed slot is located with the indexer.

In the slide retrieve or fetch mode, the finger 38 moves from between slides 24 in the cassette 22. The slide 24 is either lowered into the pocket 46 within the finger 38 by the indexer or the finger 38 and pocket 46, rise to meet the slide. Once the slide 24 is engaged by the finger 38 and pocket 46, the arm retracts to the position where the slide is on the XY-stage 18. When the slide 24 is in the proper position the arm 16 disengages the slide 24 by lowering to a position that allows clearance between the slide 24 and the finger 38. The arm 16 moves to a home position.

The slide replace mode utilizes the arm 16 differently than the fetch mode. The exchange arm finger 38, in the engaged (up) position, moves to contact the leading edge 48 of the slide. Once contact is made, the finger 38 moves to push the slide 24 into the cassette slot 22. At the point where the slide 24 is fully inside the cassette 22, the arm motion stops and the arm 16 is retracted to a safe position.

Unique features and advantages of the present invention are as follows. The slide loader instrument system adapts to any standard microscope without modification or interference with normal optical functioning of the microscope. There is a simple, single arm transport mechanism with low cost and high reliability. There is two-cassette access without the need for additional motion axes. The dual function exchange arm has a short lift travel distance which greatly simplifies the system.

The exchange arm is integrated with the XY-stage. The integration allows for the use of the X-axis and Y-axis during the slide transfer. The handler system does not interfere with the operation of the microscope. No modifications to the microscope are necessary.

All motor driven axes have closed loop encoder feedback for high reliability. The cassette mount cradle features a spring-loaded lever assembly to make slide exchange easy, but still holds the cassette firmly avoiding upset. The slide cassettes have a retainer that is used when transporting the cassettes. The retainer prevents the slides from falling out of the cassette accidentally.

The system design is modular. This allows for the addition of other automation features such as focus control unit 108 which controls focus motor 110 and objective turret changer control unit 112 which controls turret motor 114, filter wheels and illumination control. Integrated, optional operator keypad is available for system setup and operation. The use of the optional keypad reduces the software burden for the host application.

The operator interface includes an XYZ joystick used for the robotics and manual operation of the XY-stage. The slide holder is finished with a wear resistant, low friction coating to increase lifetime and reduce slide jamming. The slide holder features angled undercuts to hold the slide flat as well as laterally. There is a random slide access, whereby any slide can be accessed in any order. The slide handler instrument can be used for slide sorting by allowing any slide to be placed in any available cassette slot, as well as slide inspection and measurement.

Accordingly, while a few embodiments of the present invention have been shown and described, it is to be understood that many changes and modifications may be made thereunto without departing from the spirit and scope of the invention as defined in the appended claims.

What is claimed is:

1. An automated slide loader cassette for a microscope comprising
    a slide cassette indexer for containing a plurality of microscope slides;
    a slide exchange arm for gripping a microscope slide within said indexer and for transporting said slide to said microscope for observation and for transporting said slide after observation to return said slide back into said indexer; and
    an XY-stage for moving said slide exchange arm between said indexer and said microscope;
    said indexer, said arm, and said XY-stage are connected together and integrated into one unitary modular instrument that can be moved from one microscope to another.

2. The automated slide loader cassette according to claim 1, comprising
    means for moving said slide cassette indexer along a single vertical Z-axis along which is moved a slide cassette to a proper height for transfer of each slide; and
    said slide cassette indexer being mounted to a common, stable base-plate.

3. The automated slide loader cassette according to claim 2,
    wherein said base-plate also supports the microscope so that the orientation of the slide cassette indexer and the microscope remains fixed; and
    said means for moving said slide cassette indexer comprises a motor and a motor driven leadscrew with mechanical limits at either end of travel of said slide cassette indexer.

4. The automated slide loader cassette according to claim 1, further comprising
    means for temporarily mounting the XY-stage to the microscope so that there is no interference with any optical operation of the microscope; and
    means for moving said XY-stage in an X-axis direction and means for moving the XY-stage in a Y-axis direction.

5. The automated slide loader cassette according to claim 1,
    wherein the XY-stage has an integrated, spring loaded slide retention device that locates a slide at a fixed position; and
    said retention device being actively disengageable by mechanical linkage when the XY-stage moves along X-axis direction to a slide exchange position.

6. The automated slide loader cassette according to claim 1, comprising
    means for mounting the slide exchange arm to the XY-stage; and
    said slide exchange arm has a distal finger that manipulates the slide to remove said slide from the cassette indexer and to transfer the slide into a proper position on the XY-stage and subsequently to return the slide back into the cassette indexer.

7. The automated slide loader cassette according to claim 6,
    wherein said slide exchange arm has means for moving said arm along a long travel axis that is parallel to the X-axis of the XY-stage; and said long travel axis is defined as the radius R-axis; and
    said slide exchange arm has means for moving said arm along a short lift travel axis that tilts said arm to completely disengage the slide; and this lift travel tilt axis is the T-axis.

8. The automated slide loader cassette according to claim 7,
    wherein said T-axis has two defined positions which are engaged and disengaged;
    said slide exchange arm being driven in the R-axis direction by a motor and a motor driven belt with end-limits; and said T-axis movement of the slide exchange arm is actuated by mechanical linkage to coordinated motion from the XY-stage X-axis.

9. The automated slide loader cassette according to claim 1, comprising
a plurality of microscope slides.

10. The automated slide loader cassette according to claim 9,
in combination with a microscope; and said microscope for individually viewing said plurality of slides one at a time.

11. The automated slide loader cassette according to claim 1,
wherein the slide cassette contains two shelves;
the microscope slide is supported by the two shelves; each shelf has a lip; and each lip has a thickness and each shelf has a thickness;
each lip prevents the microscope slide from creeping out from the cassette either during transfer or by system vibration; and the thickness of each lip is from 1.2 to 1.5 times greater than the thickness of each shelf.

12. An automated slide loader cassette in combination with a microscope comprising
a microscope for individually viewing a plurality of slides one at a time;
a slide cassette indexer for containing a plurality of microscope slides;
a slide exchange arm for gripping a microscope slide within said indexer and for transporting said slide to said microscope for observation and for transporting said slide after observation to return said slide back into said indexer;
an XY-stage for moving said slide exchange arm between said indexer and said microscope; and
a computer controller for controlling the XY-stage;
said indexer, said arm and said XY-stage are connected together and integrated into one unitary modular instrument that can be moved from one microscope to another.

13. The automated slide loader cassette combination according to claim 12, comprising
means for moving said slide cassette indexer along a single vertical Z-axis along which is moved a slide cassette to a proper height for transfer of each slide; and
said slide cassette indexer being mounted to a common, stable base-plate.

14. The automated slide loader cassette combination according to claim 13,
wherein said base-plate also supports the microscope so that the orientation of the slide cassette indexer and the microscope remains fixed; and
said means for moving said slide cassette indexer comprises a motor and a motor driven leadscrew with mechanical limits at either end of travel of said slide cassette indexer.

15. The automated slide loader cassette combination according to claim 12, further comprising
means for temporarily mounting of the XY-stage to the microscope so that there is no interference with any optical operation of the microscope; and
means for moving said XY-stage in an X-axis direction and a means for moving the XY-stage in a Y-axis direction.

16. The automated slide loader cassette combination according to claim 12,
wherein the XY-stage has an integrated, spring loaded slide retention device that locates a slide at a fixed position; and
said retention device being actively disengageable by mechanical linkage when the XY-stage moves along an X-axis direction to a slide exchange position.

17. The automated slide loader cassette combination according to claim 12, comprising
means for mounting the slide exchange arm to the XY-stage; and
said slide exchange arm has a distal finger that manipulates the slide to remove said slide from the cassette indexer and to transfer the slide into a proper position on the XY-stage and subsequently to return the slide back into the cassette indexer.

18. The automated slide loader cassette combination according to claim 17,
wherein said slide exchange arm has means for moving said arm along a long travel axis that is parallel to the X-axis of the XY-stage; and said long travel axis is defined as the radius R-axis; and
said slide exchange arm has means for moving said arm along a short lift travel axis that tilts said arm to completely disengage the slide; and this lift travel tilt axis is the T-axis.

19. The automated slide loader cassette combination according to claim 18,
wherein said T-axis has two defined positions which are engaged and disengaged;
said slide exchange arm being driven in the R-axis direction by a motor and a motor driven belt with end-limits; and
said T-axis movement of the slide exchange arm is actuated by mechanical linkage to coordinated motion from the XY-stage X-axis.

20. The automated slide loader cassette combination according to claim 12, comprising
a plurality of microscope slides.

21. The automated slide loader cassette combination according to claim 12,
wherein the slide cassette contains two shelves;
the microscope slide is supported by the two shelves; each shelf has a lip; and each lip has a thickness and each shelf has a thickness;
each lip prevents the microscope slide from creeping out from the cassette either during transfer or by system vibration; and the thickness of each lip is from 1.2 to 1.5 times greater than the thickness of each shelf.

* * * * *